United States Patent
Potyrailo et al.

(10) Patent No.: US 7,271,913 B2
(45) Date of Patent: Sep. 18, 2007

(54) SENSOR SYSTEMS AND METHODS FOR REMOTE QUANTIFICATION OF COMPOUNDS

(75) Inventors: Radislav Alexandrovich Potyrailo, Niskayuna, NY (US); William Guy Morris, Rexford, NY (US); Scott Martell Boyette, New Hope, PA (US)

(73) Assignee: General Electric Company, Niskayuna, NY (US)

( * ) Notice: Subject to any disclaimer, the term of this patent is extended or adjusted under 35 U.S.C. 154(b) by 576 days.

(21) Appl. No.: 10/915,890

(22) Filed: Aug. 12, 2004

(65) Prior Publication Data

US 2005/0111001 A1    May 26, 2005

Related U.S. Application Data

(63) Continuation-in-part of application No. 10/723,534, filed on Nov. 24, 2003.

(51) Int. Cl.
G01N 21/00 (2006.01)
G01N 2/00 (2006.01)
G01N 21/59 (2006.01)

(52) U.S. Cl. ............. 356/440; 356/246; 422/82.05

(58) Field of Classification Search .............. None
See application file for complete search history.

(56) References Cited

U.S. PATENT DOCUMENTS

| | | | |
|---|---|---|---|
| 4,774,315 A | 9/1988 | Miller | |
| 5,028,690 A | 7/1991 | Gallucci | |
| 5,043,203 A | 8/1991 | Fyvie et al. | |
| 5,356,668 A | 10/1994 | Paton et al. | |
| 5,644,017 A | 7/1997 | Drumright et al. | |
| 5,668,202 A | 9/1997 | Hirata et al. | |
| 5,892,577 A | 4/1999 | Gordon | |
| 6,011,618 A | * 1/2000 | Iwata et al. | ............ 356/237.2 |
| 6,327,031 B1 | 12/2001 | Gordon | |
| 6,342,349 B1 | 1/2002 | Virtanen | |

(Continued)

FOREIGN PATENT DOCUMENTS

EP    1 189 062    3/2002

(Continued)

OTHER PUBLICATIONS

"USCD Scientists Develop Novel Way to Screen Molecules Using Conventional CDs and Compact Disk Players," Science and Engineering UCSD Press Release, Aug. 20, 2003.

(Continued)

Primary Examiner—Gregory J Toatley, Jr.
Assistant Examiner—Juan D Valentin, II
(74) Attorney, Agent, or Firm—Shawn A. McClintic; William E. Powell, III

(57) ABSTRACT

A system and method employing optical disc drives for quantitative analysis of physical, chemical and biochemical parameters are provided. The system includes a robotic arm for transmitting a disc including at least one sensor spot through a variety of stations that include dipping the disc into a source of a compound, removing excess amounts of the source, optically scanning the disc, and discarding the disc. The optical drive may be a stand-alone reader in communication with an external computing device. The output of the optical scan may be transmitted from the optical scanner to the computing device via universal serial bus, Ethernet interface, or wireless connection.

45 Claims, 21 Drawing Sheets

U.S. PATENT DOCUMENTS

| | | | |
|---|---|---|---|
| 6,500,547 | B1 | 12/2002 | Potyrailo et al. |
| 6,630,995 | B1 * | 10/2003 | Hunter .................... 356/237.5 |
| 6,946,399 | B1 * | 9/2005 | Lorimer ...................... 438/704 |
| 7,089,075 | B2 * | 8/2006 | Hasan ........................ 700/121 |
| 7,092,337 | B2 * | 8/2006 | Butler et al. ............. 369/53.22 |
| 7,110,094 | B2 * | 9/2006 | Gordon ........................ 356/73 |
| 2002/0173040 | A1 | 11/2002 | Potyrailo et al. |

FOREIGN PATENT DOCUMENTS

| | | |
|---|---|---|
| WO | 98/12559 | 3/1998 |
| WO | 99/35499 | 7/1999 |
| WO | WO 2004106925 A2 * | 12/2004 |

OTHER PUBLICATIONS

"Molecular Screening on a Compact Disc," La Clair et al., Org. Biomol. Chem. 2003 1 (Advance Article) (Abstract).

"Molecular Screening on a Compact Disc," La Clair et al., Org. Biomol. Chem. 2003 1 (Advance Article) (Paper).

"Microfabricated Centrifugal Microfluidic Systems: Characterization and Multiple Enzymatic Assays," Duffy et al. Anal. Chem. 71:4669-4678 (1999).

"Molecular Screening on a Compact Disc," La Clair et al., Org. Biomol. Chem. 2003, 1:3244-3249.

* cited by examiner

SENSOR SYSTEMS AND METHODS FOR REMOTE QUANTIFICATION OF COMPOUNDS

CROSS REFERENCE TO RELATED APPLICATIONS

This is a continuation-in-part application of U.S. application Ser. No. 10/723,534, filed Nov. 24, 2003, the subject matter of which is incorporated herein by reference in its entirety.

BACKGROUND

This disclosure relates generally to analytical instrumentation systems, and more particularly, to systems and methods for quantifying compounds in fluids, such as gases, vapors, and liquids, and solids.

Sensor methods and devices for quantifying volatile and nonvolatile compounds in fluids are known in the art. Typically, quantification of these parameters is performed using dedicated sensor systems that are specifically designed for this purpose. These sensor systems operate using a variety of principles including electrochemical, optical, acoustic and magnetic. Alternatively, a variety of colorimetric liquid and solid reagents are available to perform visual evaluation of color change.

In the art, CD/DVD drives were suggested for conducting optical inspection of biological, chemical, and biochemical samples. However, to make them useful for detection of parameters not related to digital data stored on optical media, the optical system of the drives must be modified. An optical disc drive described in U.S. Pat. No. 5,892,577 is modified to obtain the information related to chemical and biochemical detection. This modification included an addition of one or two optical detectors that are used for transmission measurements. An original optical detector of the drive is used to read digital addresses on the disc associated with an analyte-sensitive spot. Added detectors operating in transmission mode provide information on the sample to be inspected. This information from the additional detectors can be quantitative with 256 grey levels.

For operation of such a modified optical disc drive, special optical discs are prepared. Such discs have a semi-reflective layer to reflect a portion of light to one detector and transmit a portion of light to another detector, as disclosed in U.S. Pat. No. 6,327,031.

U.S. Pat. No. 6,342,349 describes another optical-drive-based measurement system. In this system, analyte-specific signal elements are disposed with the optical disc's tracking features. Thus, the analyte-specific signal elements are readable by the optics used for tracking, although modified or additional optics elements are added. For the system to be applicable, a signal responsive moiety is of a small size, compatible with the size of the focused light beam of the optical drive and is reflective. Most preferably, the signal response moiety is a gold microsphere with a diameter between 1 and 3 micrometers. The assay type used in this optical detection system is of a binary nature (see U.S. Pat. No. 6,342,349, col. 15, lines 23-37) and is not easily emendable to quantitative analysis based on light absorbance, reflection, scatter, or other optical phenomena.

Another method has also been described to screen the recognition between small molecule ligands and biomolecules using a conventional CD player. A procedure was developed to attach ligands to the reading face of a CD by activating the terminus of polycarbonate, a common polymer composite within the reading face of the CD. Displays were generated on the surface of a CD by printing tracks of ligands on the disc with an inkjet printer. Using this method, discs were created with entire assemblies of ligand molecules distributed into separate blocks. A molecular array was developed by assembling collections of these blocks to correlate with the CDROM-XA formatted data stored within the digital layer of the disc. Regions of the disc containing a given ligand or set of ligands were marked by its spatial position using the tracking and header information. Recognition between surface expressed ligands and biomolecules was screened by an error determination routine (see Org. Biomol. Chem., 1, 3244-3249 (2003)).

Different types of analyte-specific signal elements are also known in the art. International patent application WO 99/35499 describes the use of colloidal particles, microbeads, and the regions generated by a corrosive attack on one or several layers of a compact disc as a result of binding between the target molecule and its non-cleavable capture molecule. The analyte-specific signal elements can be arranged in arrays, for example, combinatorial arrays (International patent application WO 98/12559). In addition to solid and gel types of analyte-specific signal elements, other types include liquid-containing regions (Gamera Bioscience System, see: Anal. Chem. 71 4669-4678 (1999)).

In a related art, remote automated sensors have been employed for a variety of applications ranging from the cost-effective monitoring of industrial processes, to the determination of chemicals toxic to humans at locations of interest, to analysis of processes in difficult-to-access locations. For these and many other reasons, a wide variety of sensors have been reported that operate in the automatic, unattended mode. For example, sensors were reported that operate remotely for detection of toxic vapors, uranium ions, and many other species. Measurements have also been done remotely in space on manned and unmanned spacecraft.

Remote measurement systems can be initiated and monitored via the Internet where a dedicated sensor is connected to a computer that receives commands via the Internet as described in U.S. Pat. Nos. 5,931,913, 6,002,996, 6,182,497, 6,311,214, 6,332,193, 6,360,179, 6,405,135, and 6,422,061. Generally, upon receiving a command, the computer initiates a sensor that is specifically designed to perform a sensing function and is connected to the computer. The sensor performs the measurement, the computer receives the sensor signal, and optionally, sends the signal back to a control station.

Automated computer-controlled sensors for remote unattended operation known in the art have two distinct components. These components are (1) a sensor itself and (2) a computer. These components are designed and built to perform initially separate functions and further are combined into a remotely operated sensor system. The limitations of such approach include development of a sensor itself, and its adaptation for computer control.

SUMMARY

A system and method employing optical disc drives for quantitative analysis of chemical and biochemical parameters are provided. According to one aspect, an optical media sensor system is provided for quantifying compounds. The system includes a robotic arm capable of transporting an optical medium between a plurality of stations, and an optical media reader capable of determining a quantity of at least one compound or physical property on the optical medium.

According to another aspect, an optical media sensor system for quantifying compounds is provided. The system includes a robotic arm capable of transporting an optical medium between a first station at which the robotic arm picks up optical medium in succession and a second station at which the optical medium is exposed to a source of the compounds. The robotic arm also transports the optical medium between a third station at which excess amounts of the source are removed, a fourth station at which the optical medium is read, and a fifth station at which the optical medium is discarded. The system also includes an optical media reader capable of determining a quantity of at least one compound on the optical medium at the fourth station.

According to another aspect, a system for optically determining the quantity of one or more compounds on one or more sensors is provided. The system includes a computing device and an optical media drive (such as DVD, CD, BLU-RAY DISC®, super audio CD, hybrid disc, and any other drive that reads optical media articles) located external to the computing device. The DVD drive is capable of optically reading an optical medium upon which are located the one or more sensors. The DVD drive is in communication with the computing device.

According to another aspect, a method for determining the quantity of one or more compounds on one or more sensors is provided. The method includes remotely retrieving an optical medium having one or more sensors from a first station, exposing the optical medium to a source of the compounds at a second station, and reading the optical medium in an optical drive.

According to another aspect, a method for determining the quantity of one or more compounds on one or more sensors is provided. The method includes remotely retrieving an optical medium having one or more sensors from a first station, exposing the optical medium to a source of the compounds at a second station, removing excess amounts of the source from the optical medium at a third station, and reading the optical medium in an optical drive at a fourth station.

According to another aspect, a method for optically determining the quantity of one or more compounds on one or more sensors is provided. The method includes optically scanning an optical medium, having at least one sensor sensitive to the presence of a compound, in a stand-alone optical drive, and transmitting the output of the optical scan from the stand-alone optical drive to a computing device for quantifying the compound.

BRIEF DESCRIPTION OF THE DRAWINGS

The above and other aspects, features, and advantages of the invention will become more apparent in light of the following detailed description when taken in conjunction with the accompanying drawings.

DETAILED DESCRIPTION OF PREFERRED EMBODIMENTS

Preferred embodiments of the present invention will be described herein below with reference to the accompanying drawings. In the following description, well-known functions or constructions are not described in detail to avoid obscuring the invention in unnecessary detail.

This invention uses an optical disc drive as a sensor readout device and provides quantitative information from an optical disc about variable optical properties of predetermined spatial locations on the disc. These predetermined spatial locations on the optical disc are defined as "sensor spots". Depending on the application, the sensor spots are responsive to physical, chemical, biochemical, and other changes in the environment. The light that propagates through the sensor spot, reflects off the optical media's reflective layer, and propagates back through the sensor spot prior to detection and is modulated proportional to the change of various conditions, for example, a change proportional to the concentration of a compound affecting the sensor spot. The light intensity will be read by the optical disc drive to quantify the amount of the compound. In addition to intensity changes, other light parameters are used for quantitation in the sensor spot such as light polarization state, and the direction of the propagation of light after interaction with the sensor spot.

Figure 1:
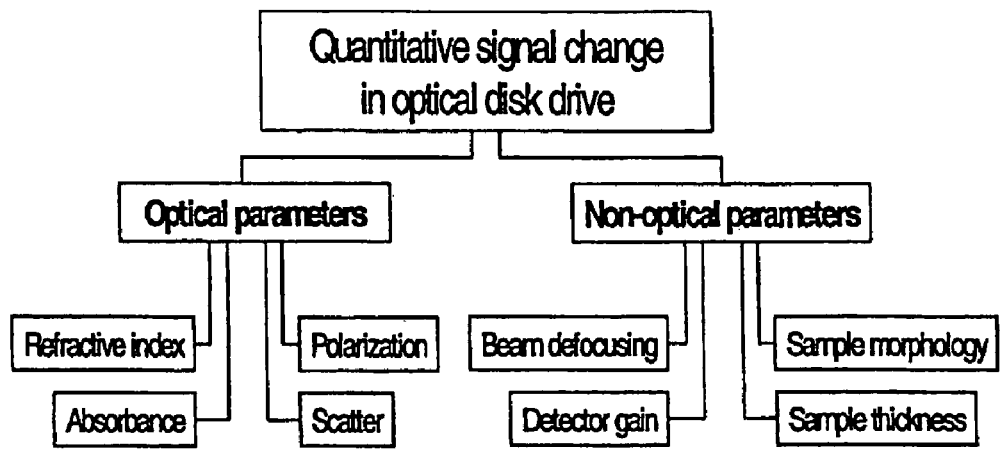
FIG. 1 illustrates parameters that quantitatively affect a level of signal produced from a disc including a physical and chemical/biochemical sensor.

A variety of physical, chemical, biochemical and environmental parameters quantitatively affect the level of signal produced by the sensor spots on an optical disc. These parameters can be grouped as optical and non-optical parameters, as shown in FIG. 1. Optical parameters include optical properties of the measured sample, for example, its refractive index, absorbance, polarization, scatter, and any other optical parameters of the sample or induced by the sample on the sensor spots. The non-optical parameters are those contributing from, for example, sample thickness and sample morphology, as well as from the performance of the optical disc drive, such as beam defocusing and detector gain.

By altering the optical and non-optical properties, sensor spots can be employed to detect non-chemical parameters of the environment. Non-limiting examples of these parameters include physical, mechanical, dielectric, electric, magnetic, and other non-chemical parameters. More specific examples are temperature, viscosity, pressure, oxidation-reduction potential, permeability, molecular weight, porosity, hydrophobicity, surface energy, solution conductivity, etc.

Changes in refractive index can be produced by different amounts of swelling of a sensor material upon an uptake of a sample, when a liquid of a refractive index different from that of the sample is diffused into the sample. For example, swelling of poly (hydroxy-ethyl) methacrylate upon exposure to water changes the refractive index as a function of exposure time. Additionally, changes in refractive index can be produced as a result of a performance test of a sample such as aging, weathering, temperature annealing, etc. The sample's refractive index may change as a function of these parameters.

Changes in polarization can be produced as a result of sorbing a solution of an optically active material into the sample film, e.g., sensor spot. For example, different concentrations of sugar in blood or other fluids can be determined from the change in the detector light intensity due to the rotation of polarization plane of the light after passing through sugar-containing film.

Changes in light scatter can be produced as a result of sorbing a solution containing light scattering material into the sensor spot. For example, different concentrations of particulate in wastewater can be determined from the change in the detector light intensity due to the scatter of light after passing through a sample film, e.g., sensor spot. As another example, hydrolytic stability of samples can be determined from the change in the detector light intensity due to the scatter of light after passing through the sample film upon exposure to high temperature, humidity, and/or pressure. As a further example, sample abrasion resistance can be determined from the change in the detector light intensity due to the scatter of light after passing through the sample film upon exposure of the samples to abrasion test such as oscillating sand, Taber test, sand-blast, or others.

Figure 2A:
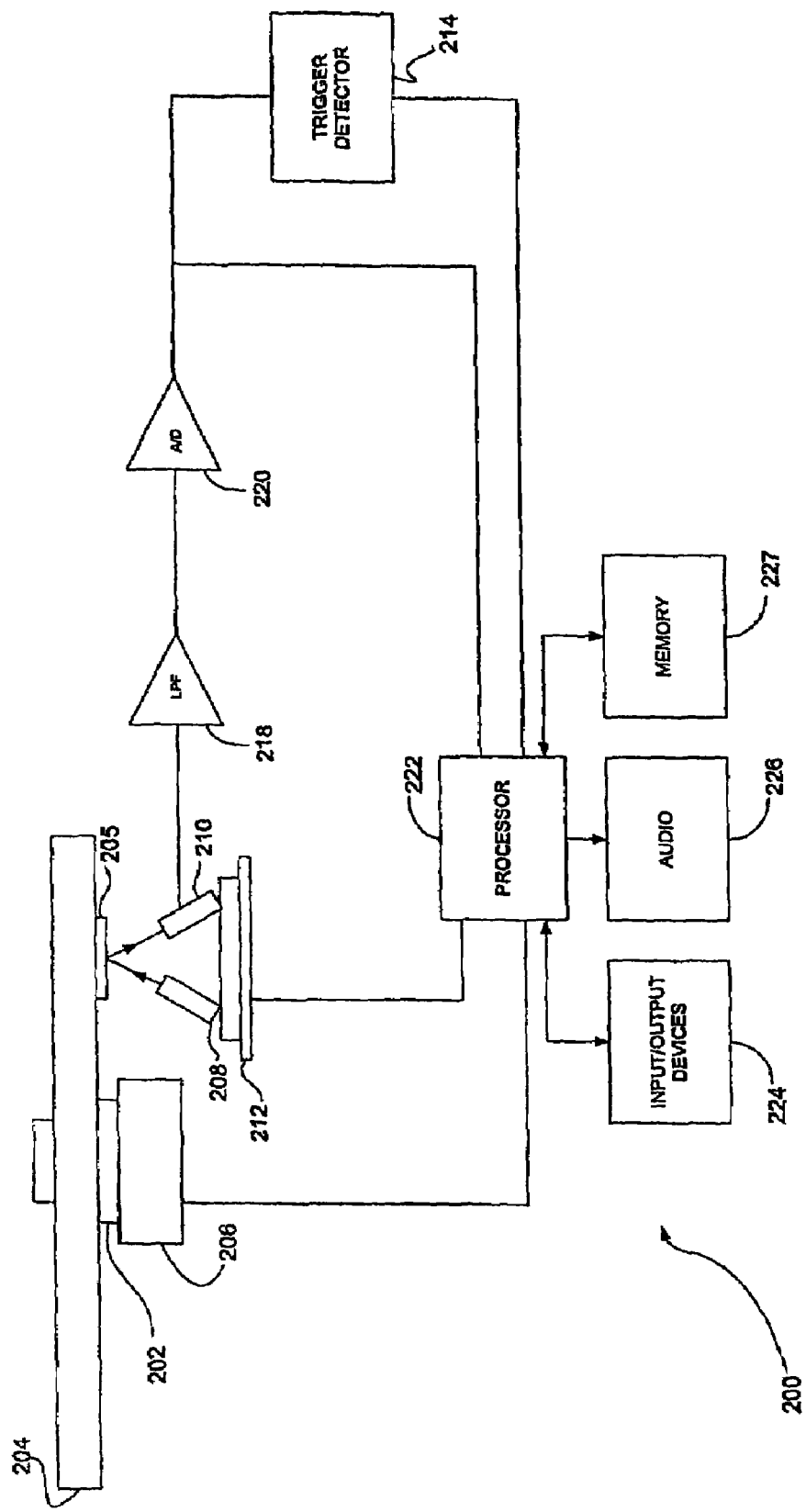
FIG. 2A is a block diagram of an exemplary system for quantification of physical parameters, chemical and biochemical volatile and nonvolatile compounds using trigger-based detection.

Referring to FIG. 2A, the sensor system 200 includes a disc drive 202 for supporting a disc 204 including a plurality of sensor spots 205. The disc drive 202 is coupled to a drive motor 206 for rotating the disc 204 when in operation. The optical disc drive further includes a light source, e.g., a laser, for directing light onto a readable surface of the disc 204 and an optical pickup 210 for detecting light reflected from the disc 204. The light source 208 and optical pickup 210 are mounted on a tracking mechanism 212 to move the light source 208 and optical pickup 210 in an outward direction from a center of the disc while in a read operation.

As in a conventional optical disc drive, the system 200 includes a trigger detector 214 coupled to the optical pickup 210 to determine when a change in level of light has occurred, e.g., when light is reflected from a pit or a land, to generate a 0 or 1 data stream. Unlike in conventional drives, drive 200 includes an analog-to-digital converter A/D 220 coupled to the optical pickup 210 for measuring intensity values of the reflected light as an RF signal. Outputs of the trigger detector 214 and the analog-to-digital converter 220 are sent to processor 222 for rendering measured intensity values on an input/output device 224, such as a display, or via an audio means 226. The system 200 will further include a memory 227, such as a random access memory (RAM), read only memory (ROM), etc, for storing data and application programs. Detector intensity is defined as the RF signal generated by the intensity of reflected light captured by the optical pickup 210.

The data contained in the raw RF signal (about 10 MHz) shows up as noise when sampled at 200 khz in the analog-to-digital converter 220. Because the processor 222 is interested only in the average levels in a baseline signal and peaks of the measured signal, this noise can be further reduced by filtering via filter 218 or by averaging multiple waveforms.

Figure 2B:
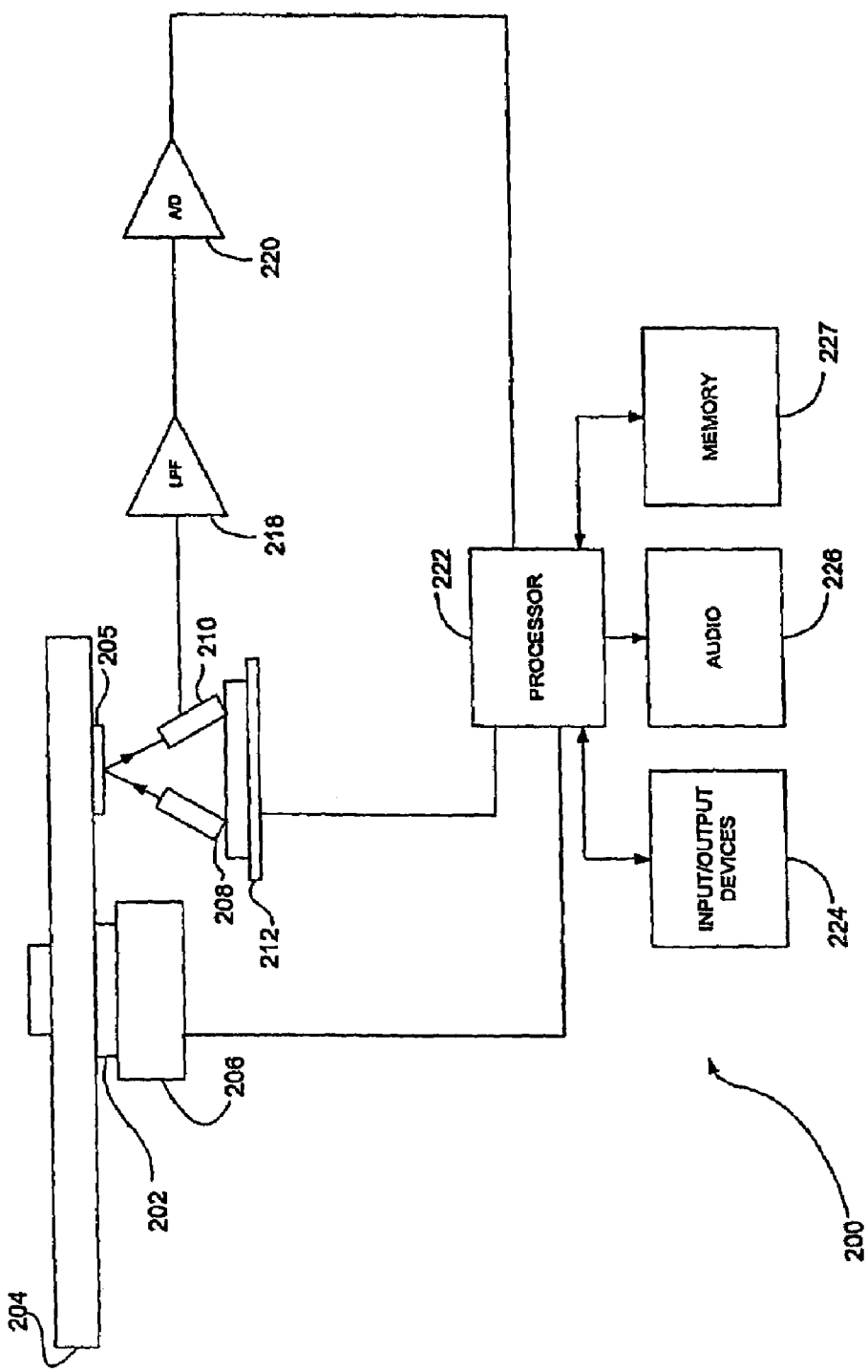
FIG. 2B is a block diagram of an exemplary system for quantification of physical parameters, chemical and biochemical volatile and nonvolatile compounds using a non-trigger-based detection.

Referring to FIG. 2B, a further embodiment of the sensor system 200 includes a disc drive 202 for supporting a disc 204 including a plurality of sensor spots. The disc drive 202 is coupled to a drive motor 206 for rotating the disc 204 when in operation. The optical disc drive further includes a light source 208, e.g., a laser, for directing light onto a readable surface of the disc 204 and an optical pickup 210 for detecting light reflected from the disc 204. The light source 208 and optical pickup 210 are mounted on a tracking mechanism 212 to move the light source 208 and optical pickup 210 in an outward direction from a center of the disc while in a read operation.

Unlike in conventional drives, drive 200 of FIG. 2B includes an analog-to-digital converter A/D 220 coupled to the optical pickup 210 for measuring intensity values of the reflected light as an RF signal. Output from the analog-to-digital converter 220 is sent to processor 222 for rendering measured intensity values on a display 224 or via an audio means 226.

Furthermore, the system may be employed to detect phase changes of materials deposited onto the disk. The system 200 may include an inductive heater that heats a specific sensor spot on the optical disc. The sensor spot is heated and a phase change is indicated by a change in light reflection, turbidity, etc. Phase detection will work with solid materials coated in the sensor spot, or in contained solutions, e.g., for dew-point/bubble-point detection. Similarly, plasticization, crystallization, dissolution and/or freezing will be detectable.

It is to be understood that embodiments of the invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM) and a read only memory (ROM) 227 and input/output (110) device(s) 224 such as keyboard, cursor control device (e.g., a mouse) and display device. An internal system clock is also provided for performing temporal analysis as well as automating drive movements at specific times. The computer platform also includes an operating system and micro instruction code. The various processes and functions described herein may either be part of the micro instruction code or part of the application program (or a combination thereof) which is executed via the operating system. In addition, various other peripheral devices may be connected to the computer platform such as an additional storage device and printing device.

For example, the analog signal, e.g., measured intensity of light, is coupled to an input of an analog-to-digital conversion circuit such as a National Instruments DAQCard model AI-16XE-50, and the digital data is read into a personal computer. Alternatively, the analog signal may be acquired from an analog-to-digital circuit inside a modified optical drive or externally from, for example, a digital oscilloscope.

It is to be further understood that, because some of the constituent system components and method steps depicted in the accompanying figures may be implemented in software, the actual connections between the system components (or the process steps) may differ depending upon the manner in which embodiments of the invention are programmed.

Figure 3A:
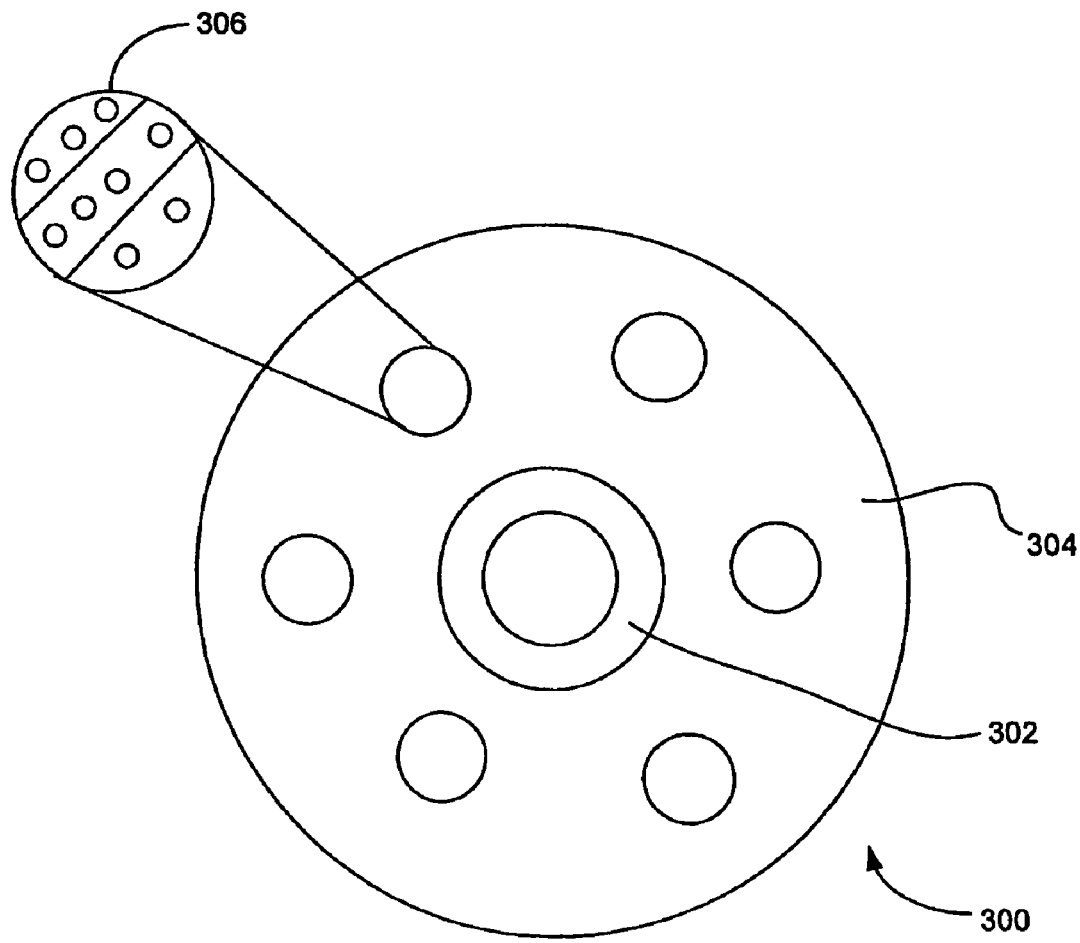
FIG. 3A is a top plan view of a disc including a plurality of sensor spots.

Referring to FIG. 3A, an exemplary optical disc 300 is shown. The disc 300 generally is constructed from an injection-molded piece of clear polycarbonate plastic which is impressed with microscopic bumps arranged as a single, continuous spiral track of data as is known in the art. The bumps will form a series of pits and lands, i.e., non-bump areas, which will be encoded as digital data, i.e., 0's and 1's when the disc is read in the drive. A reflective metallic layer, typically aluminum, is sputtered onto the plastic covering the bumps, and then, in the case of compact discs (CDs) a thin acrylic layer is coated over the aluminum to protect it. In the case of DVDs, the metalized substrate is bonded to another polycarbonate substrate using a UV-curable adhesive.

Figure 3B:
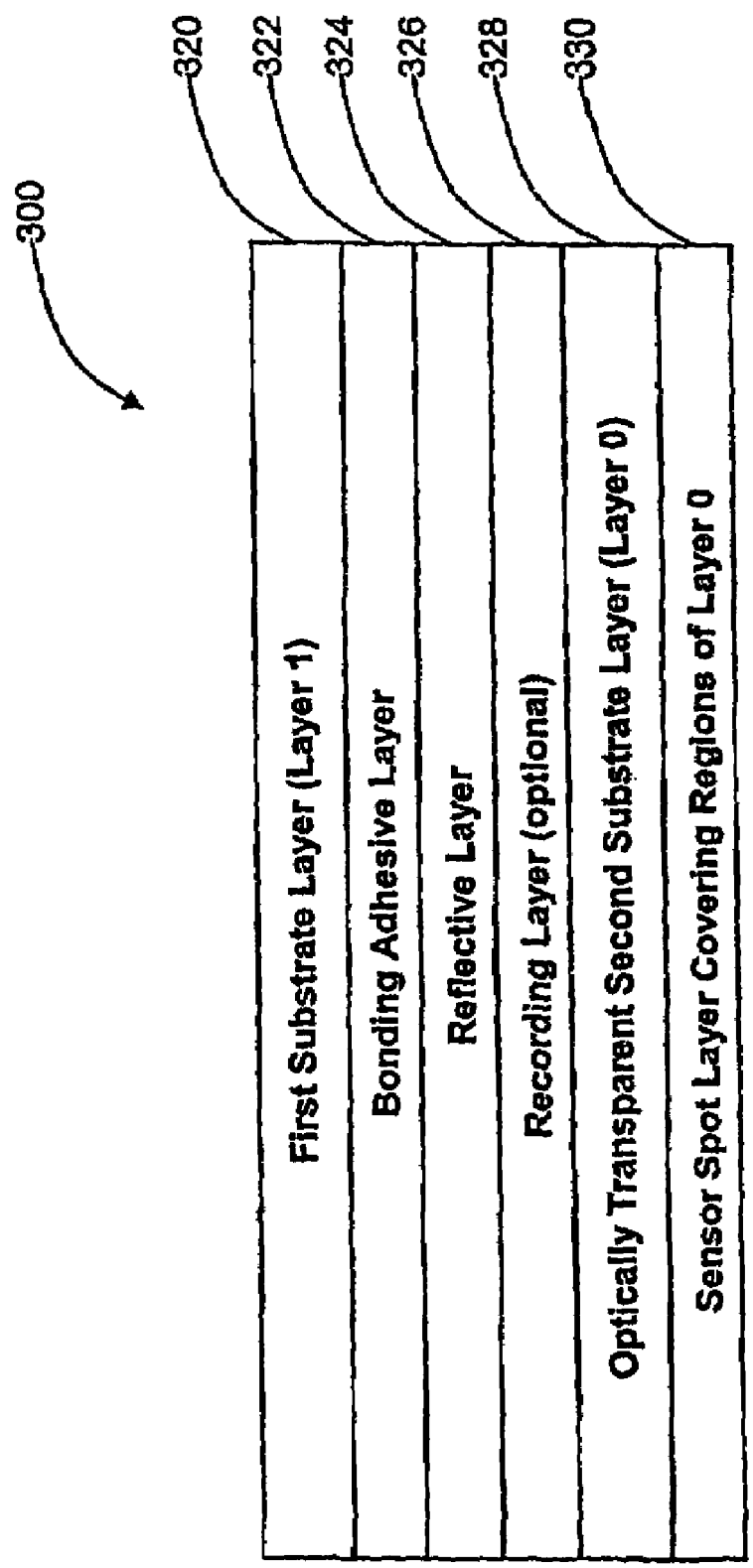
FIG. 3B is a cross sectional view of an optical disc containing a sensor spot.

FIG. 3B is a cross sectional view of the optical disc containing a sensor region.

Referring to FIG. 3B, in various embodiments, the optical disc 300 includes a plurality of layers. These layers include, but are not limited to, a first substrate layer 320 (substrate layer 1) comprising a thermoplastic, such as a polycarbonate or the like; an optically transparent second substrate layer 328 (substrate layer 0) also comprising a thermoplastic, such as a polycarbonate or the like; a reflective layer 324 comprising a metal, such as Al, Ag or Au, or the like; optionally, either a data layer comprising regions of pits and lands molded into the second substrate and/or a recording layer 326 comprising a recordable material, such as phthalocyanine or the like, or a re-writable material, such as an magneto-optic (MO) material, a phase-change material, a chalcogenide or the like; a bonding adhesive layer 322; and a sensor spot layer 330 covering regions of the second substrate (layer 0). Each of the layers is described in greater detail herein below.

It should be noted that, although preferred layer combinations are illustrated and described herein, other layer combinations will be readily apparent to those of ordinary skill in the art and are contemplated by the present invention.

The plastic employed for both the first substrate 320 and second substrate 328 should be capable of withstanding subsequent processing parameters (e.g., application of subsequent layers) such as sputtering temperatures of about room temperature (about 25° C.) up to about 150° C., and subsequent storage conditions (e.g., in a hot car having temperatures up to about 70° C.). That is, it is desirable for the plastic to have sufficient thermal and mechanical stability to prevent deformation during the various layer deposition steps as well as during storage by the end-user. Possible plastics include thermoplastics with glass transition temperatures of about 100° C. or greater, with about 125° C. or greater preferred, about 140° C. or greater more preferred, and about 200° C. or greater even more preferred (e.g., polyetherimides, polyetheretherketones, polysulfones, polyethersulfones, polyetherethersulfones, polyphenylene ethers, polyimides, polycarbonates, etc.); with materials having glass transition temperatures greater than about 250° C. more preferred, such as polyetherimide in which sulfonedianiline or oxydianiline has been substituted for m-phenylenediamine, among others, as well as polyimides, combinations comprising at least one of the foregoing plastics, and others. Generally, polycarbonates are employed.

Some possible examples of first substrate and second substrate materials include, but are not limited to, amorphous, crystalline, and semi-crystalline thermoplastic materials such as: polyvinyl chloride, polyolefins (including, but not limited to, linear and cyclic polyolefins and including polyethylene, chlorinated polyethylene, polypropylene, and the like), polyesters (including, but not limited to, polyethylene terephthalate, polybutylene terephthalate, polycyclohexylmethylene terephthalate, and the like), polyamides, polysulfones (including, but not limited to, hydrogenated polysulfones, and the like), polyimides, polyether imides, polyether sulfones, polyphenylene sulfides, polyether ketones, polyether ether ketones, ABS resins, polystyrenes (including, but not limited to, hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including, but not limited to, polymethylmethacrylate (PMMA), methyl methacrylate-polyimide copolymers, and the like), polyacrylonitrile, polyacetals, polycarbonates, polyphenylene ethers (including, but not limited to, those derived from 2,6-dimethylphenol and copolymers with 2,3,6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, and tetrafluoroethylenes (e.g., Teflons).

The optical disc 300, e.g., data storage media, can be produced by first forming the substrate material using a conventional reaction vessel capable of adequately mixing various precursors, such as a single or twin-screw extruder, kneader, blender, or the like. The extruder should be maintained at a sufficiently high temperature to melt the substrate material precursors without causing decomposition thereof. For polycarbonate, for example, temperatures in a range between about 220° C. and about 360° C. can be used, and preferably in a range between about 260° C. and about 320° C. Similarly, the residence time in the extruder should be controlled to minimize decomposition. Residence times of up to about 2 minutes (mm) or more can be employed, with up to about 1.5 mm preferred, and up to about 1 mm especially preferred. Prior to extrusion into the desired form (typically pellets, sheet, web, or the like), the mixture can optionally be filtered, such as by melt filtering, the use of a screen pack, or combinations thereof, or the like, to remove undesirable contaminants or decomposition products.

Once the plastic composition has been produced, it can be formed into the substrate using various molding techniques, processing techniques, or combinations thereof. Possible techniques include injection molding, film casting, extrusion, press molding, blow molding, stamping, and the like. Once the substrate has been produced, additional processing, such as electroplating, coating techniques (e.g., spin coating, spray coating, vapor deposition, screen printing, painting, dipping, and the like), lamination, sputtering, and the like, as well as combinations comprising at least one of the foregoing processing techniques, may be employed to dispose desired layers on the substrate. Typically, the substrate has a thickness of up to about 600 microns.

In recordable media, the data are encoded by laser, which illuminates an active data layer that undergoes a phase change, thus producing a series of highly-reflecting or non-reflective regions making up the data stream. In these formats, a laser beam first travels through an optically transparent substrate before reaching the data layer. At the data layer, the beam is either reflected or not, in accordance with the encoded data. The laser light then travels back through the optically transparent substrate and into an optical detector system where the data are interpreted. Thus, the data layer is disposed between the optically transparent substrate 328 and the reflective layer 324. The data layer(s) for an optical application typically is pits, grooves, or combinations thereof on the substrate layer. Preferably, the data layer is embedded in the substrate surface. Typically, an injection molding-compression technique produces the substrate where a mold is filled with a molten polymer as defined herein. The mold may contain a preform, insert, etc. The polymer system is cooled and, while still in at least partially molten state, compressed to imprint the desired surface features, for example, pits and grooves, arranged in spiral concentric or other orientation onto the desired portions of the substrate, i.e., one or both sides in the desired areas.

Possible data layers for magnetic or magneto-optic applications may comprise any material capable of storing retrievable data and examples include, but are not limited to, oxides (such as silicone oxide), rare earth elements, transition metal alloys, nickel, cobalt, chromium, tantalum, platinum, terbium, gadolinium, iron, boron, others, and alloys and combinations comprising at least one of the foregoing, organic dyes (e.g., cyanine or phthalocyanine type dyes), and inorganic phase change compounds (e.g., TeSeSn, InAgSb, and the like).

Optionally, protective layer(s), which protect against dust, oils, and other contaminants, may be provided on the sensor spot layer. The protective layer can have a thickness of greater than about 100 microns ($\mu$) to less than about 10 Angstroms (Å), with a thickness of about 300 Å or less preferred in some embodiments, and a thickness of about 100 Å or less especially preferred. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising at least one of the foregoing materials.

Optionally, dielectric layer(s), which are typically disposed on one or both sides of the data layer and are often employed as heat controllers, can typically have a thickness of up to or exceeding about 1,000 Å and as low as about 200 Å or less. Possible dielectric layers include nitrides (e.g., silicon nitride, aluminum nitride, and others); oxides (e.g., aluminum oxide); sulfides (e.g. zinc sulfide); carbides (e.g., silicon carbide); and combinations comprising at least one of the foregoing materials, among other materials compatible within the environment and preferably not reactive with the surrounding layers.

The reflective layer(s) 324 should have a sufficient thickness to reflect a sufficient amount of energy (e.g., light) to enable data retrieval. Typically the reflective layer(s) can have a thickness of up to about 700 Å or so, with a thickness in a range between about 300 Å and about 600 Å generally preferred. Possible reflective layers include any material capable of reflecting the particular energy field, including metals (e.g., aluminum, silver, gold, silicon, titanium, and alloys and mixtures comprising at least one of the foregoing metals, and others).

The adhesive layer 322 can adhere any combination of the above-mentioned layers. The adhesive layer can comprise any material that does not substantially interfere with the transfer of light through the media from and to the data retrieval device (e.g., that is substantially transparent at the wavelength of light utilized by the device, and/or which allows a reflectivity from the media of about 50% or greater, with a percent reflectivity of about 65% or greater preferred and a percent reflectivity of about 75% or greater more preferred). Possible adhesive materials include UV materials such as acrylates (e.g., cross-linked acrylates, and the like), silicon hardcoats, and the like, as well as reaction products and combinations comprising at least one of the foregoing materials. Other examples of UV materials are described in U.S. Pat. Nos. 4,179,548 and 4,491,508. Some useful monoacrylate monomers include butyl acrylate, hexyl acrylate, dodecyl acrylate and the like. Some useful polyfunctional acrylate monomers include, for example, diacrylates, triacrylates, tetraacrylates, and combinations thereof.

Although the adhesive layer may contain only one of said polyfunctional acrylate monomers, or a mixture comprising at least one of the polyfunctional acrylate monomers (and the UV light reaction product thereof), preferred coating compositions contain a mixture of two polyfunctional monomers (and the UV light reaction product thereof), preferably a diacrylate and a triacrylate (and the UV light reaction product thereof), with mono-acrylate monomers used in particular instances. Optionally, the adhesive coating can comprise nonacrylic UV curable aliphatically unsaturated organic monomers in amounts up to about 50 weight % of the uncured adhesive coating that includes, for example, such materials as N-vinyl pyrrolidone, styrene, and the like, and reaction products and combinations Comprising at least one of the foregoing materials.

The disc 300 includes a digital data section 302 and a sensor section 304 including a plurality of sensor spots 306. Since data is recorded on the spiral track from the inside of the disc to the outside, the digital data section 302 is located on the inner most part of the disc 300. The digital data section 302 may include information on the locations of the sensor spots 306, types of the sensor spots, etc.

Each sensor spot 306 covers multiple pit/land areas. This feature of the sensor region provides the ability to average signals across different regions of the same sensor spot to improve the signal-to-noise ratio, as will be described below. The term "covers" refers to the spot being located between the laser incident surface of the optical disc and the data layer containing pits and lands. The spot can be located in a coating layer not necessarily adjacent to the pit/land layer, but rather in the optical path of the laser to a specific pit/land region.

Figure 4:
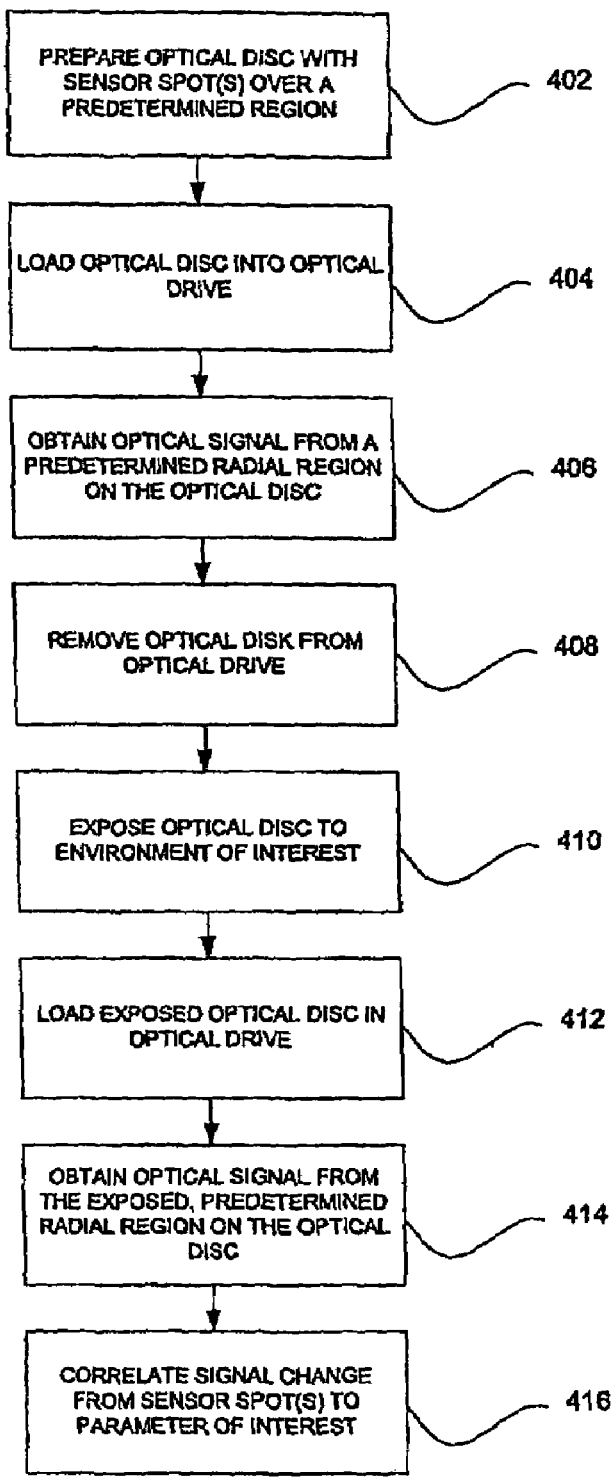
FIG. 4 is a flowchart illustrating a method for quantification of physical and chemical and biochemical volatile and nonvolatile compounds in fluids in off-line mode.

Referring to FIG. 4, a method for quantifying compounds in fluids is illustrated. Initially in step 402, an optical disc is prepared with sensor spots over a predetermined region of the optical disc. The optical disc is then loaded into the optical disc drive (step 404). The optical disc is then read via the optical disc drive to obtain a baseline reading (step 406). Next, the optical disc is removed from the optical disc drive (step 408) and it is exposed to any environment of interest (step 410). The optical disc is then again placed in the optical disc drive (step 412). The exposed optical disc is read and a signal indicative of the change in at least one optical property of a sensor spot is produced (step 414). The signal obtained from the exposed optical disc, e.g., intensity of transmitted light, is then compared to the baseline signal to determine changes in the environment of interest (step 416). Alternatively, a highly reproducible disc production method that results in acceptable disk-to-disk variation could allow the baseline reading (steps 404, 406 and 408) to be eliminated by substituting a prerecorded baseline from another disk or a prerecorded baseline stored in memory 227.

Figure 5:
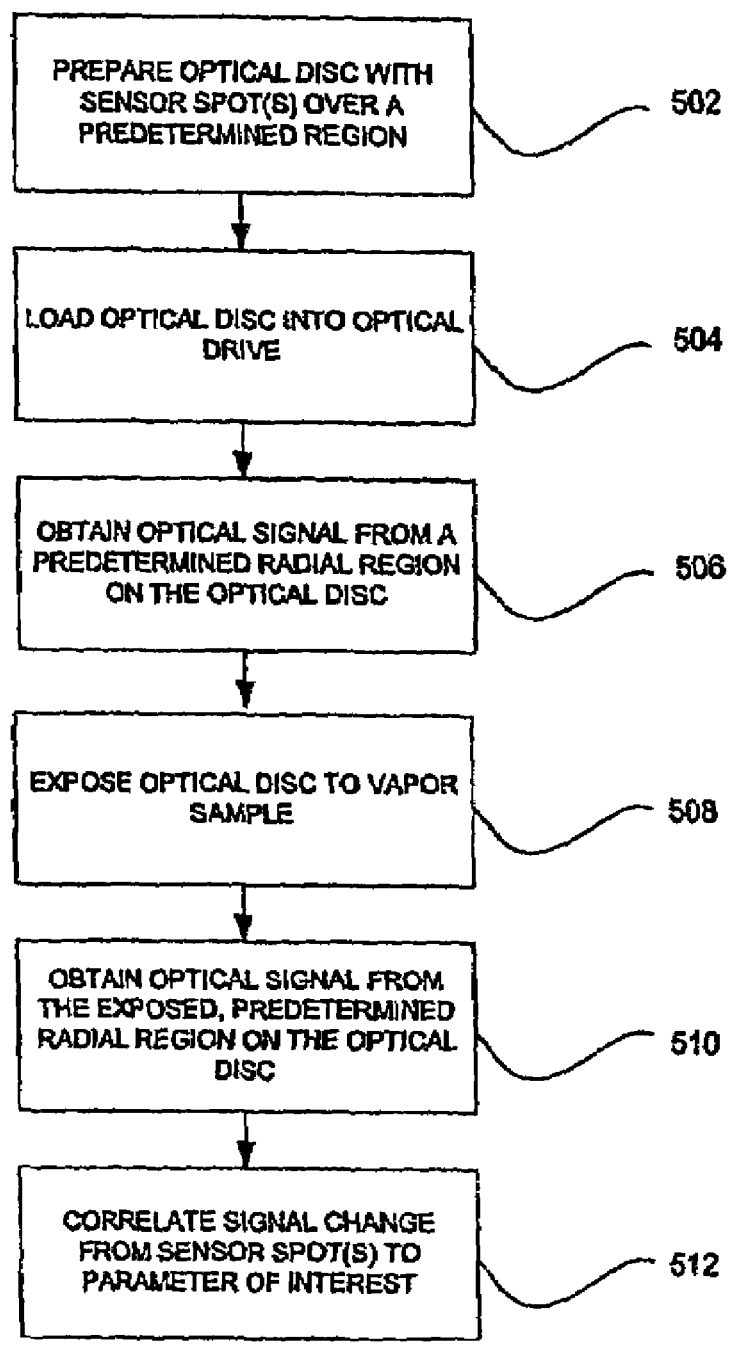
FIG. 5 is a flowchart illustrating a method for quantification of physical and chemical and biochemical volatile and nonvolatile compounds in fluids in on-line mode.

Referring to FIG. 5, a further method for quantifying compounds in fluids is illustrated. In this embodiment, the optical disc senses the environment of interest while located in the optical disc drive. Initially in step 502, an optical disc is prepared with sensor spots over a predetermined region of the optical disc. The optical disc is then loaded into the optical disc drive (step 504). The optical disc is then read via the optical disc drive to obtain a baseline reading (step 506). Next, the optical disc is exposed to a substance that is drawn through the optical disc drive (step 508). The exposed optical disc is read and a signal indicative of the change in at least one property of a sensor spot is produced (step 510). The signal obtained from the exposed optical disc e.g., intensity of transmitted light, is then compared to the baseline signal to determine changes in the environment of interest (step 512). Alternatively, a highly reproducible disc production method that results in acceptable disk-to-disk variation could allow the baseline reading (step 506) to be eliminated by substituting a prerecorded baseline from another disk or a prerecorded baseline stored in memory 227.

According to the above method, the optical disc drive 200 may include a vapor induction port for drawing a vapor including a compound into the drive to expose the vapor to the optical disc. Optionally, a fan may be employed to facilitate drawing the vapor into the induction port.

Figure 6:
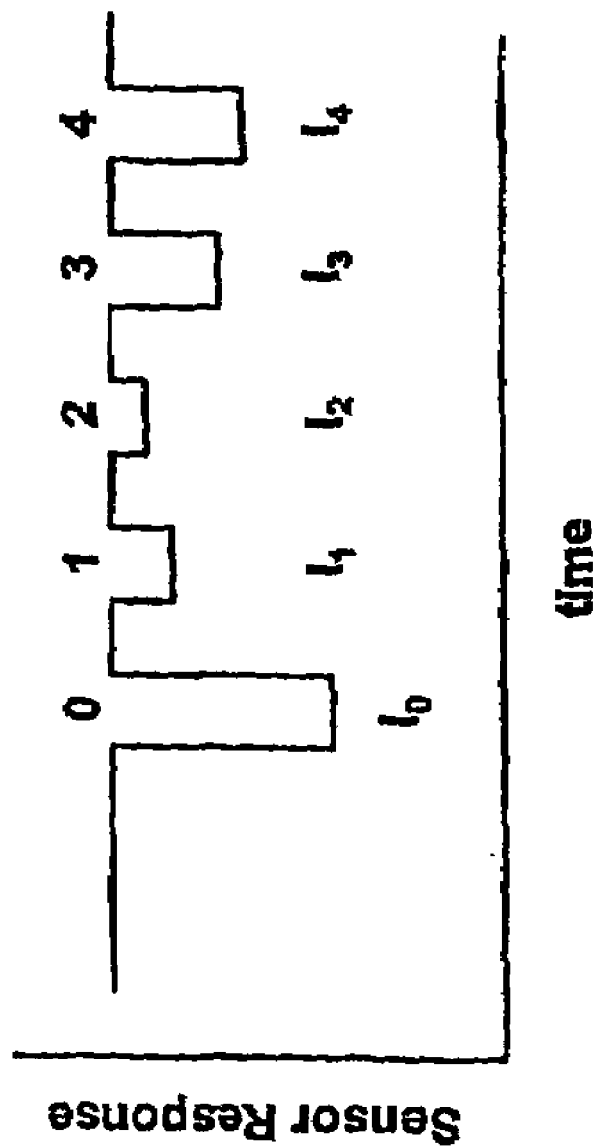
FIG. 6 is a graph illustrating quantitative signal detection using a trigger-based method where time indicates the relative distance on the optical disc.

A data acquisition method for obtaining the optical signal known in the art is based on a triggered data acquisition method, as illustrated in FIG. 6. According to this method, a single waveform begins at a trigger mark, $I_0$. The length (for example, in microseconds) of a single waveform should be sufficient to capture all of the sensor spots before the next trigger mark. A signal from the trigger mark must be stronger than any of the sensor spots. Otherwise, false triggering can occur on a spot, and the subsequent averaging of multiple waveforms will result in inaccuracies. A total of n individual waveforms can be recorded and then averaged. The trigger mark can also serve as an internal reference mark. The internal reference mark can provide reference information about the drive and the disk, for example, changes in operating temperature due to heating of the drive, ambient conditions during measurements. Also, such an internal reference mark can serve as an indicator of exposure time of the sensor spots on the disc to the environment of interest, provided that the trigger mark was also exposed to this environment. In operation, the trigger mark changes its signal intensity depending to the measured parameter. The trigger level $I_0$ is selected to be larger than any anticipated signal from any of sensor spots.

Figure 7:
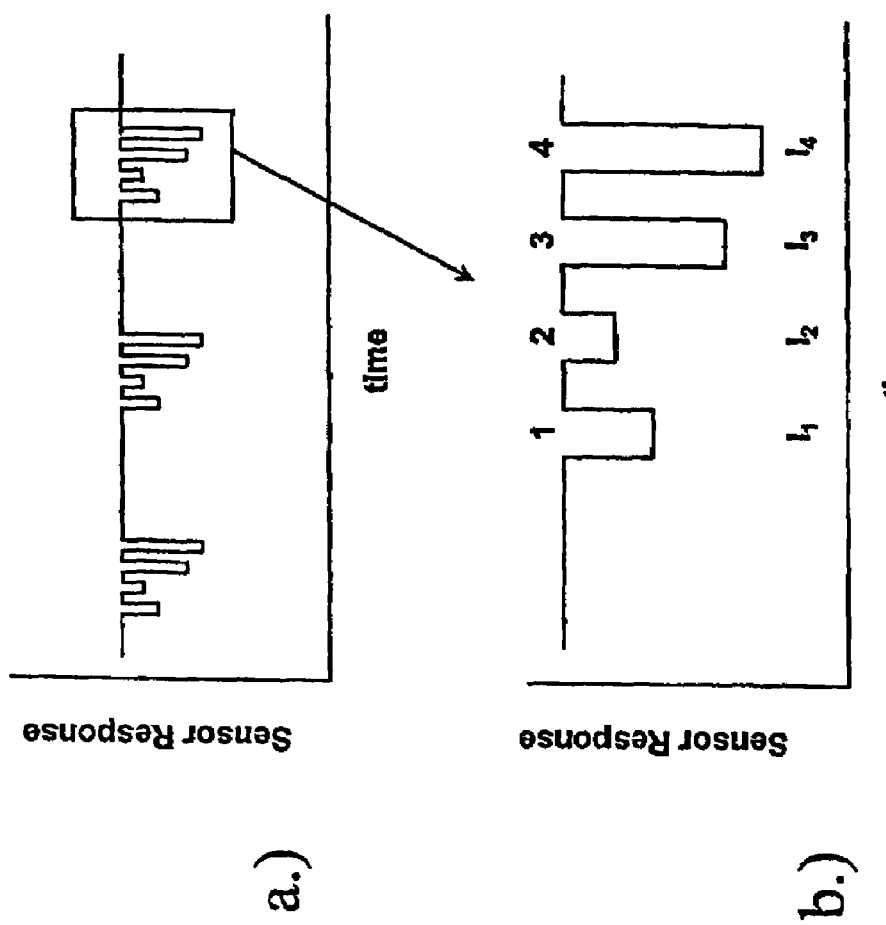
FIG. 7 is a graph illustrating quantitative signal detection using a non-trigger-based method where time indicates the relative distance on the optical disc.

The system of the present invention may collect a data stream starting at any random location. For example, after the disc table of contents is read, the processor can instruct the drive to access data at any random logical block address on the disc. In this non-trigger-based method, data collection does not depend on a trigger and can be initiated at any time. A data stream is captured continuously for n revolutions of the disc. There could be over 100,000 data points in the data stream. The method locates a pattern within the data stream (FIG. 7(A)), and extracts subsets of data (FIG. 7(B)), each of which corresponds to a single revolution. The subsets are summed or averaged. If incomplete subsets exist at the start or end of the data stream, they are discarded. An important advantage of the non-trigger method of the present invention is that the system will not hang while waiting for a trigger mark. Trigger marks may not be necessary if other features, e.g., data patterns, adequately identify subsets.

Various experiments were preformed using various compounds and reactants, the results of which will be described below.

Figure 8:
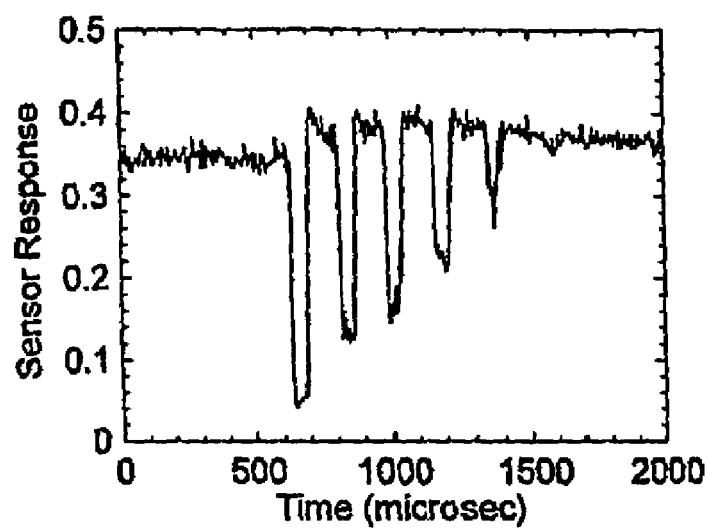
FIG. 8 is a graph illustrating quantitative signal detection of an unexposed disc where time in microseconds indicates the relative distance on the optical disc.

For demonstration of quantitative detection, regions of different grey scale were produced on a surface of an optical disc. These regions were designed to be insensitive to environmental conditions and to serve as reference regions. Measurements were performed across different grey-scale regions simultaneously. For the measurements, a CD/DVD combination drive, e.g., Pioneer Model 115, was used. Data acquisition was performed using a single channel of a digital oscilloscope, e.g., Digital Phosphor Oscilloscope, Tektronix Model TDS 5054, with the sampling rate of less than 50 MHz and with the averaging of 100 waveforms. FIG. 8 shows typical collected waveforms from these multiple regions. These data demonstrate the capability of the optical drive to detect different gray scale regions. The intensity of detector signal is proportional to the grey scale.

Figure 9:
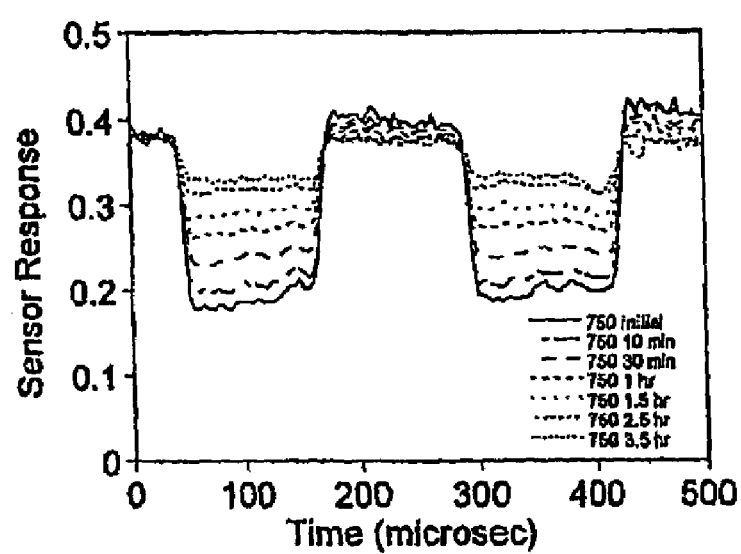
FIG. 9 is a graph illustrating time-dependent change in optical signal of two adjacent sensor spots on an optical disc surface exposed to 0.03% bleach where time in microseconds indicates the relative distance on the optical disc.

For detection of oxidative species in water, thin film regions (e.g., sensor spots) containing methylene blue (MB) dye were coated onto the surface of a DVD, e.g., an optical disc. The signals from these regions were measured before the sensor spots were exposed to water containing oxidative species. The several sensor spots were then exposed to a water solution containing about 0.03% of bleach. As controls, several MB sensor spots were exposed to pure water with no oxidant. Measurements of oxidation were periodically done after 0.17, 0.5, 1.0, 1.5, 2.5, and 3.5 h. FIG. 9 illustrates the time-dependent change in detector signal of two adjacent films exposed to 0.03% bleach. The signals from the control MB sensor spots exposed to water did not change.

Figure 10:
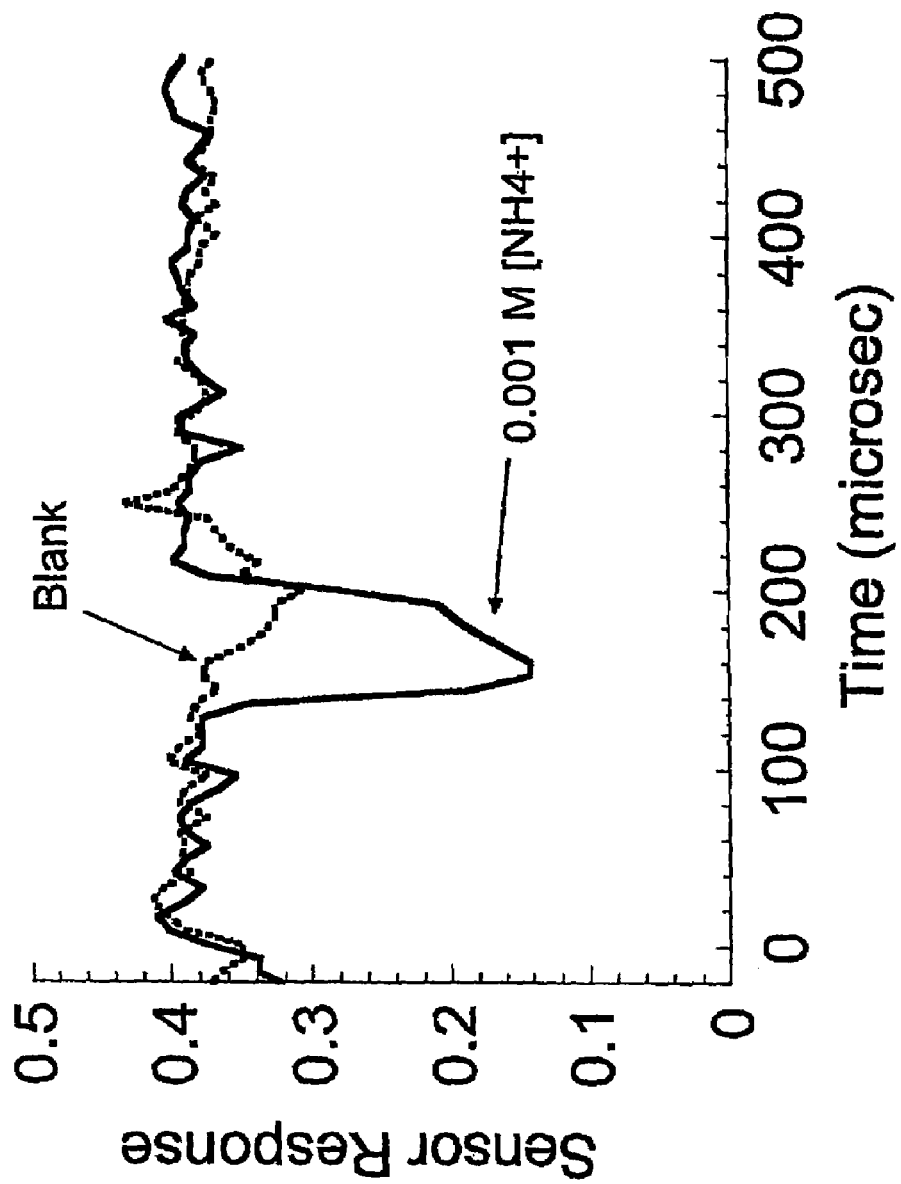
FIG. 10 is a graph illustrating changes in an optical signal of a sensor spot for detection of $NH_4+$ where time in microseconds indicates the relative distance on the optical disc.

For detection of ionic species such as $NH_4+$ in water, thin film regions (e.g., sensor spots) containing different pH dyes were coated onto the surface of a DVD, e.g., an optical disc. These dyes included bromocresol green (Aldrich, 11,435-9), bromophenol blue (Nutritional Biochemicals, 12-238), and bromocresol purple (Aldrich, 86,089-1, 90% dye content). The initial signal of the films was measured followed by the exposure of the disc to a solution containing 0.001 M of $NH_4+$. Upon removal from the solution, the disc was measured again. FIG. 10 depicts the change in detector signal of the bromocresol green film before, e.g., blank baseline, and after exposure to $NH_4+$. This figure illustrates that the sensor is detecting the presence of $NH_4+$.

Figure 11:
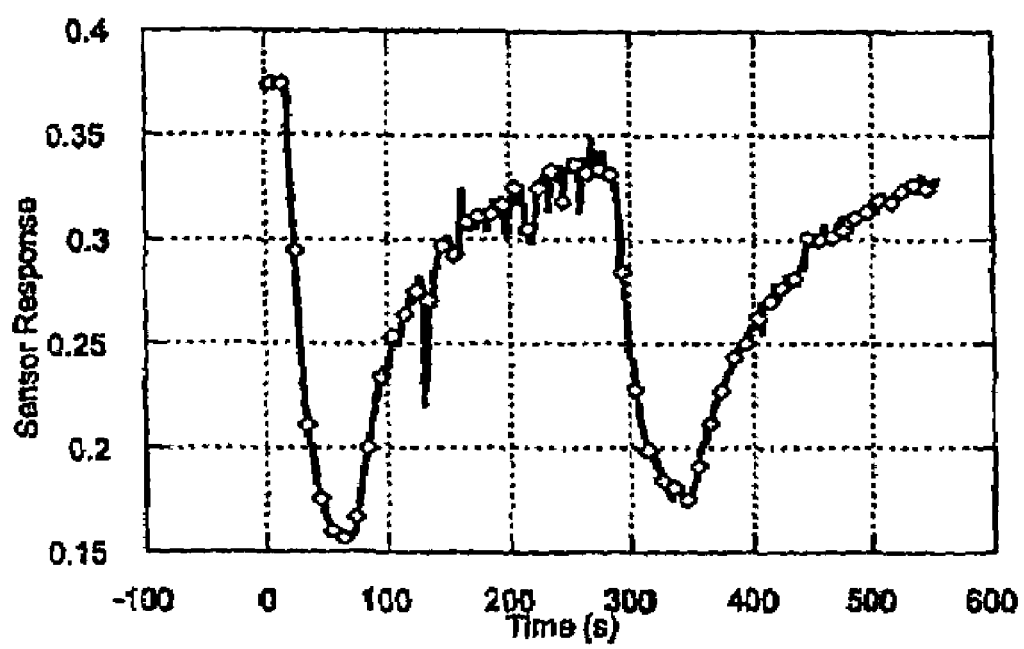
FIG. 11 is a graph illustrating on-line detection of vapors using a single sensor spot on an optical disc.

Detection of species on-line was demonstrated with an optical disc containing a sensor spot responsive to ammonia vapor. The spot was a film containing bromocresol green dye (Aldrich, 11,435-9) in a polymer matrix. The optical disc was loaded in a drive that had a vapor induction port. Ammonia vapor was delivered into the drive when the optical disc was read by the drive. The sensor spot responded to the increasing concentration of ammonia in air as shown in FIG. 11. After a period of time, the vapor flow was switched to a carrier gas without ammonia. This is evident by the increase in signal collected by the drive, i.e., the signal returned to its baseline. Another cycle was further performed starting at 290 s, showing a reversible and reproducible test spot response.

Determination of chemical composition of a fluid was performed using light-scattering detection in an optical drive. A polymer film (e.g., sensor spot) was deposited onto a DVD, e.g., an optical disc, wherein the material of the polymer film was responsive to one of the components in a sample fluid. The response of the polymer film and resulting detector signal was provided by the intensity of the light scattered in the film after exposure to a sample fluid.

Figure 12:
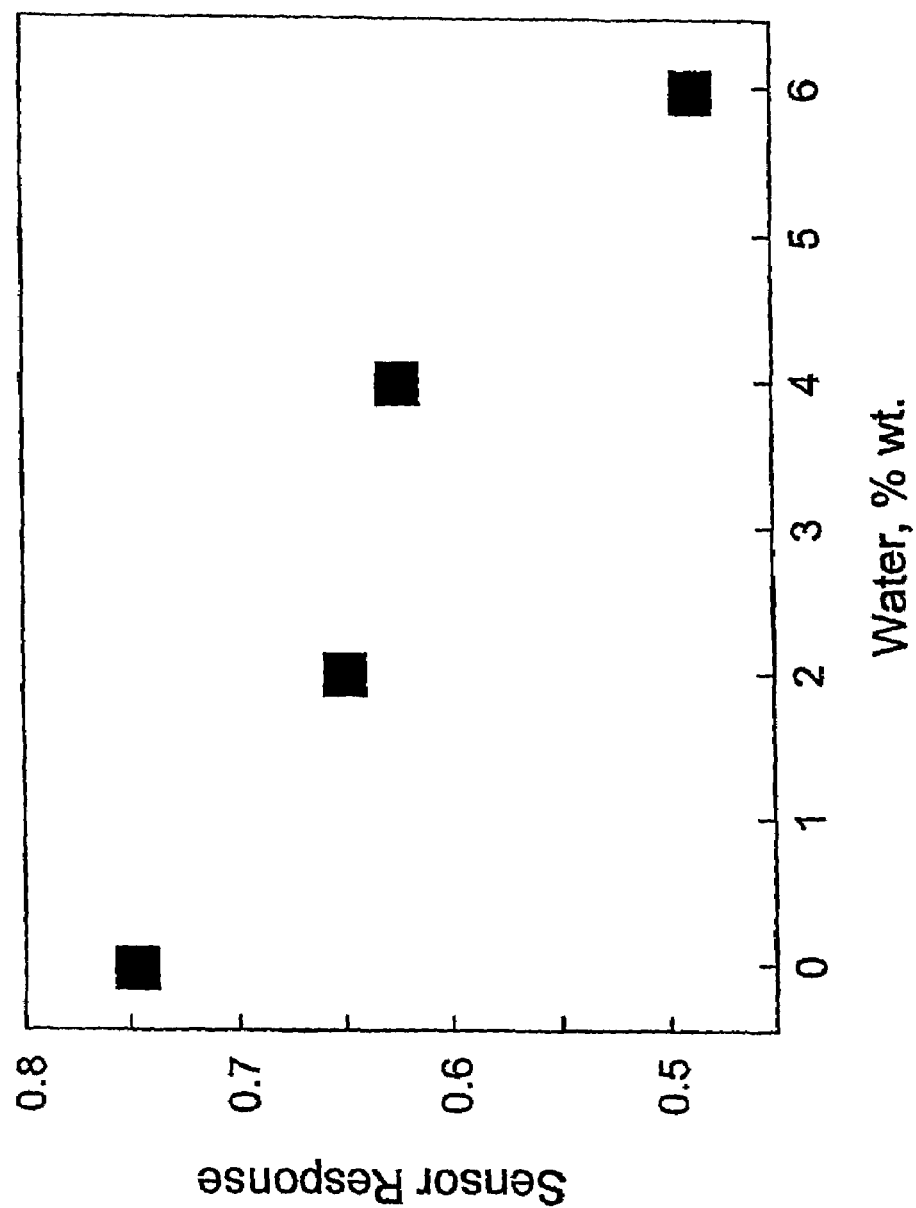
FIG. 12 is a graph illustrating a response of a DVD-based sensor to a change in chemical composition of fluid samples, wherein an amount of collected light (exposure response) is related to water content in a solvent (1-methoxy-2-propanol) as measured with poly(2-hydroxyethyl methacrylate) sensor films.

To fabricate the responsive film, poly(2-hydroxyethyl methacrylate) (obtained from Aldrich) was dissolved in an appropriate solvent (such as for example, 1-methoxy-2-propanol) at an appropriate polymer concentration to produce a transparent film. Films were produced by flow coating the polymer solution. Analyte samples were prepared with variable concentrations of an analyte of interest (water) in a non-aqueous solvent. As an example of a solvent, 1-methoxy-2-propanol was used. For quantitation of water concentration, first, the dry (unexposed) sensor films were measured with the optical drive by quantifying the detector signal. The sensor films were then exposed to varied concentrations of water/solvent compositions for 15 seconds. After each exposure, each sample fluid was removed with compressed air at ambient temperature. The sensor films were then measured by reading the DVD in the optical drive and recording the detector signal intensities from the exposed sensor spots. Results of this experiment are presented in FIG. 12. The figure indicates the magnitude of the signal change resulting from exposure of the sensor film to water-containing samples.

Various signal-processing approaches were further developed to improve signal measurement precision. The developed approaches were based on the selection of an appropriate region, position, and size around the sensor spot. The precision-improvement data analysis can include but is not limited to summing, averaging, Fourier filtering, Savitsky-Golay filtering, and any other data analysis technique known in the art.

The various methods for improvement of signal precision are summarized in Table 1.

TABLE 1

| Signal-processing Approaches | Description | Comments |
| --- | --- | --- |
| Method 1 | Signal quantification only from a small region of the sensor | Simplest data analysis algorithm |
| Method 2 | Signal quantification from an active area of sensor spot | Improves precision by summing all sensing regions |
| Method 3 | Signal quantification from the whole area of the sensor spot | Improves precision by summing all sensing regions and also inactive areas of sensor spot |

In method 1, signal quantification is acquired from only a small region of a sensor spot. Referring to FIG. 3A, sensor spot 306 covers a specific region of the optical disc. Although the data track spiraling on the disc is one continuous track, sensor spot 306 has, for example, three separate tracks transversing it. According to method 1, a signal may be quantified from only one track. This method will employ a simple data analysis algorithm resulting in less computation time and resources.

In method 2, a signal is acquired from an active area of the sensor spot, e.g. an area that demonstrates the signal change upon exposure to stimuli from the environment. Readings from the active areas are then summed.

In method 3, a signal is acquired from the whole area of the sensor spot including an inactive area. An inactive area of sensor spot is an area that has a non-representative signal change upon exposure to stimuli from the environment. An example of such area is the edge of the sensor spot where the concentration of dye or coating thickness may be much higher than in the center because of the method used to produce the sensor spots.

Figure 13:
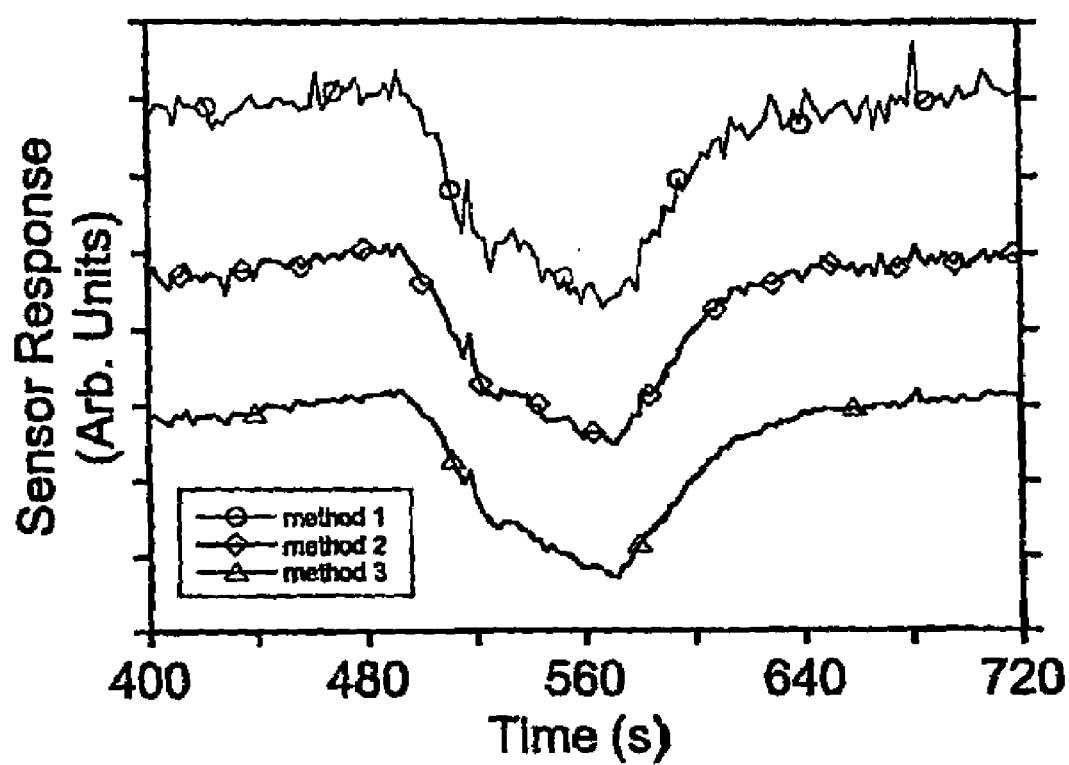
FIG. 13 is a graph illustrating improvement of signal precision in varying methods for quantifying compounds in fluids.

FIG. 13 illustrates the results of the various signal processing approaches using the same optical disc. A chemically sensitive region, e.g., sensor spot, was produced by dissolving Rhodamine 800 laser dye in Nafion and casting films onto an optical disc. Upon exposure to moisture, the absorbance of the film was changed. Signal changes of the computer optical drive sensor in the presence of different amounts of ambient water vapor around the sensor, e.g., 0% RH and approximately 22% RH are presented in FIG. 13. As shown in FIG. 13, the smallest noise in the measured signal upon exposure of the sensor to 0 and 22% RH was achieved using the data processing method 3. In this method, the signal is collected from the sensor spot and from adjacent regions in order to compensate for some jitter effects, where jitter is defined here as a random fluctuation of signal with time.

Figure 14:
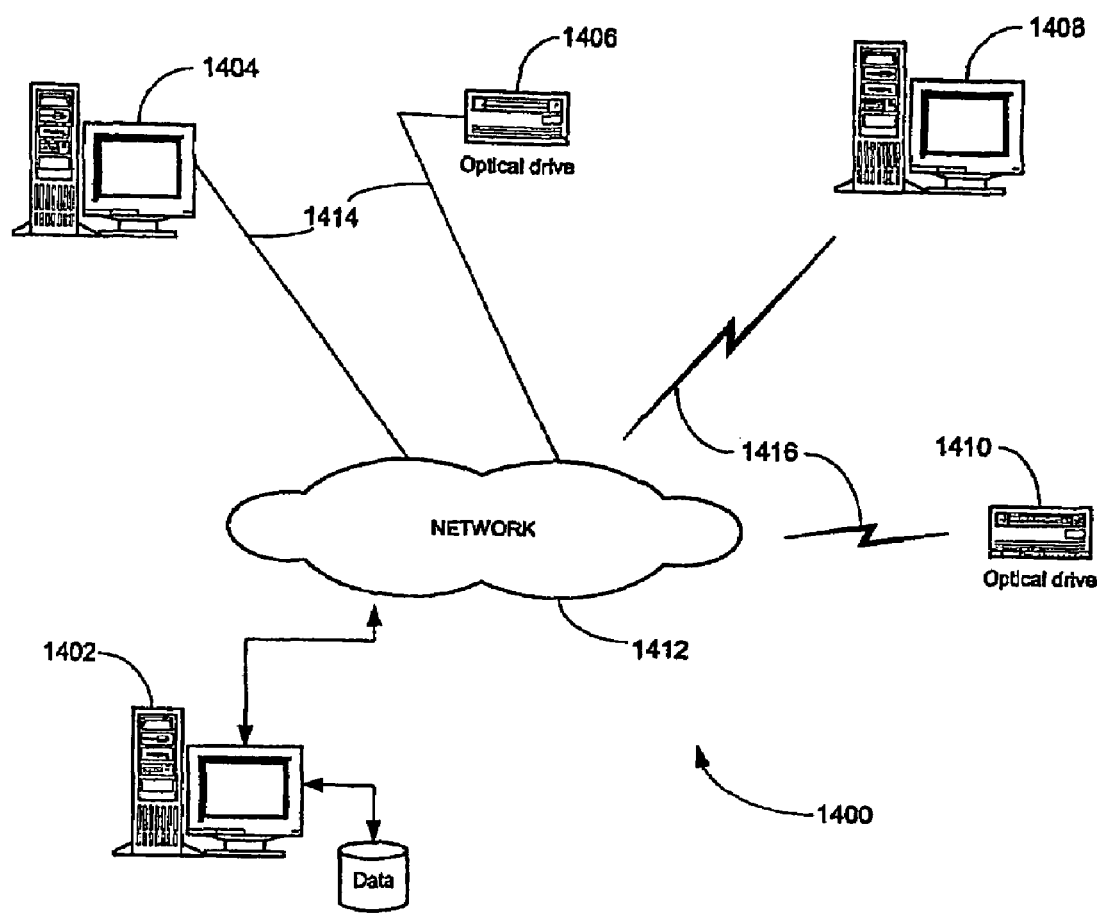
FIG. 14 is diagram of a networked sensor system.

Referring to FIG. 14, a networked sensor system 1400 is provided. The networked sensor system 1400 includes a central communication center 1402 coupled to a plurality of sensor devices 1404, 1406, 1408, 1410 via network 1412. The network 1412 may be a Local Area Network (LAN), a Wide Area Network (WAN), the Internet or any other known network for coupling a plurality of computers, servers or the like.

It is to be understood that the sensor devices are functionally similar to those described above in relation to FIGS. 2A and 2B. In one embodiment, sensor devices 1404, 1408 are optical drives mounted internal or directly connected to a computer, e.g., a server, personal computer (PC), laptop, personal digital assistant (PDA), etc. In this embodiment, the computer will perform its customary functions while the optical drive senses the environment. Additionally, the optical disc including at least one sensor spot may be removed from the computer to read other optical media.

In a further embodiment, the sensor device 1406, 1410 may be a standalone optical drive having a network interface card. In this embodiment, raw data collected by the drive may be sent to the central communication center 1402 for processing.

Similarly, a remote bus can be connected to a networking device, e.g., a hub, and provide a link to several independent stand-alone optical drives to provide multiplexed sensing on multiple drives at a single location. This system of interconnected sensor devices can be used to monitor the movement of a particular analyte across a spatial region of the location or to monitor the presence or movement of biomaterials or organisms as they move through air or vapors in a particular location or plurality of locations. For example, as different sensor devices detect a particular analyte at different times, the system 1400 may determine the direction and speed of the moving analyte.

It is to be appreciated that information collected by the remote sensor devices 1404, 1406, 1408, 1410 may be transmitted via landline 1414, cellular phone, satellite relay or other wireless communication link 1416 to the central communication center 1402.

Optionally, several optical drive sensors can be arranged in a single computer system, either connected directly to the mother board or through an external bus, e.g., a Universal Serial Bus (USB). These optical drive sensors can perform measure me its of different environmental parameters based on the use of different laser wavelengths. Available wavelengths include substantially about 650 nm and 780 nm. Additional wavelengths could be available upon further development of the optical drive technologies. For example, wavelengths at around 400 nm (BLU-RAY DISC® optical drives) are currently under development and can be easily used for the optical drive sensors.

A computer with at least one installed optical drive sensor 1404 can be used for measurements of environmental parameters. For example, concentrations of ambient chemicals can be measured with such a sensor. Any conventional computer is not hermetically sealed thus, ambient vapors may interact with the optical disc including at least one sensor spot by diffusion through the voids in the computer and optical drive housing. If needed, the number and size of these voids can be increased, or a mechanical fan can be added to promote better access of ambient vapors to the optical drive. An auxiliary automated vapor delivery system can be easily adapted for the use with the same software that operates the optical disc drive. Additionally, the whole computer can be installed in an enclosure that is selectively permeable to certain types of vapors while other types of vapors and liquids will not permeate into the enclosure. Such an option can be attractive to monitor free gases in water, e.g., chlorine.

Furthermore, a computer with at least one installed optical drive sensor 1404 can be used for measurements of biological contaminants in an environment. For example, concentrations of airborne spores or cysts, bacteria, viruses, or proteins can be measured with such a sensor. In this embodiment, the disk drive can be coated with material that gives a response to certain biomolecules of concern. This species can be whole organisms like bacterial cells, spores, or cysts, or they can be virus, or associated proteins indicative of dangerous biomaterials.

Figure 15:
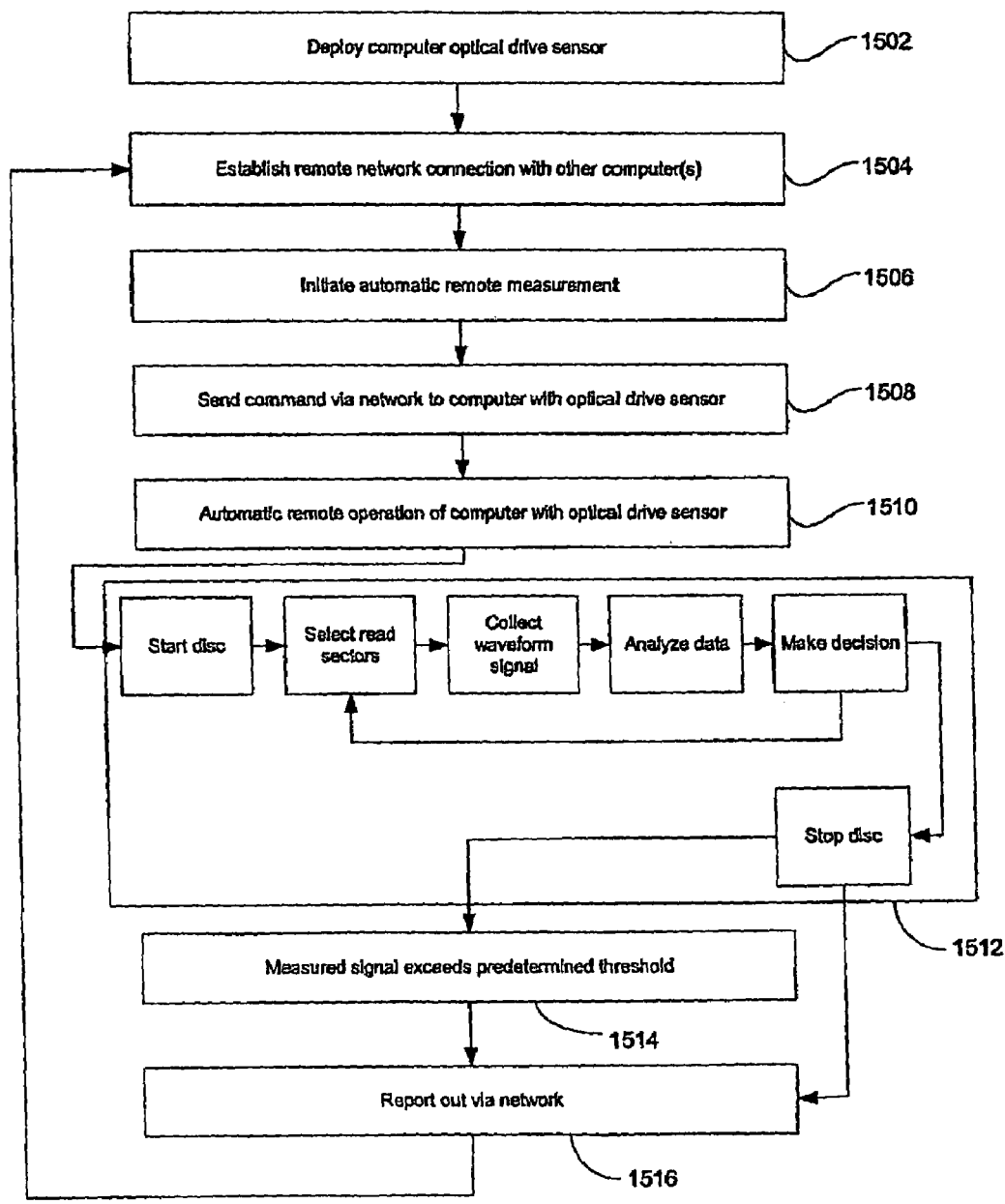
FIG. 15 is a flow chart illustrating an operation of the networked sensor system.

An operation of the automated remotely-addressable optical drive sensor is illustrated in FIG. 15. The computer optical drive sensor can be installed in a laptop or desktop personal computer or in another computer system that is capable of communicating with an optical drive. An optical disc containing environmentally sensitive regions, e.g., sensor spots, is installed into the optical drive (step 1502). A network connection is established via any known communication protocol (step 1504). Remote measurements are then initiated using any known network-supported software (step 1506), e.g., LABVIEW® commercially available from National Instruments of Austin, Tex. Upon receiving a command via the network (step 1508), the computer and/or optical drive sensor starts its automatic remote operation (step 1510).

During the sensing process (step 1512), the sensor device operates as described above in relation to FIGS. 4 and 5, for example, the software automatically selects predetermined (pre-preprogrammed) regions to scan with the optical disc drive laser. During this scan, a waveform from the detector output as a function of measurement time is recorded. This waveform is analyzed with respect to the signal intensity in predetermined location on the waveform.

Upon analysis, the signal quality is compared with the reference value that can be stored in advance in computer memory or can be provided by a signal of another region of the optical disc or from another reference disk in another drive. The signal from the sensor device is further compared with a predetermined threshold signal quality (step 1514). This predetermined threshold signal quality can be indicative of a certain level of the measured environmental parameter. The final response of the computer can be sending a status report via the network as an electronic mail or by other means (step 1516). Alternatively, such report can be sent only when the measured signal exceeds the predetermined threshold signal quality.

The networked sensor system 1400 can also monitor the rate of change in the sensor response and determine both an accelerated change in the target parameter, and conversely, a significant decrease in the target parameter. This allows the remote monitoring system 1400 to tell when an event occurs, the severity of the event, and when the event is no longer outside a pre-established operating range. Additionally, interpretation of rates of change in the target parameter can be used to provide information about the periodicity of the event, a key element in troubleshooting the cause of the parameter variance. This is particular useful for unattended systems that have discontinuous events.

Quantitative detection of chemical species, via experimentation, was achieved with an optical drive sensor installed in a personal computer at a remote location.

Depending on the chemically sensitive reagents distributed in the sensing regions on the optical disc, different types of chemicals can be monitored. An example of this sensing strategy was demonstrated for detection of humidity. For demonstration, the changes in this chemical concentration were produced by bubbling different amounts of dry air through liquid water. Vapor introduction was controlled by the same software, e.g. LABVIEW®, that was also used to operate the optical drive sensor. Additionally, this data acquisition program permits network communication between computers and remote automated monitoring and control of data acquisition parameters.

Figure 16:
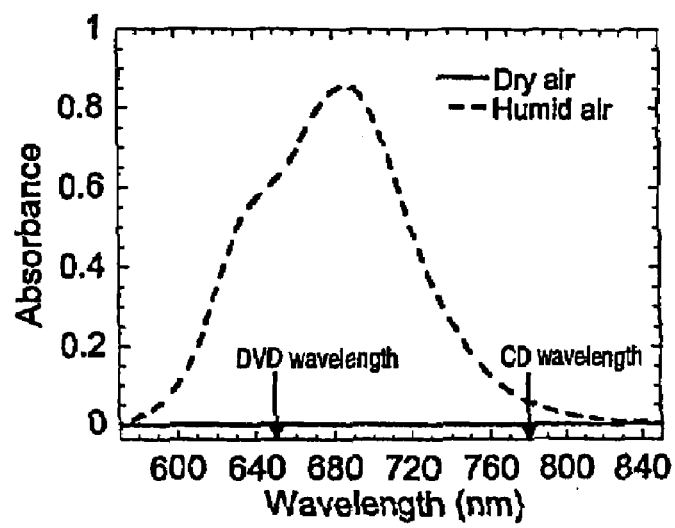
FIG. 16 is a graph illustrating typical absorbance of spectra of Rhodamine 800 laser dye in Nafion in a form of a cast film in dry and humid air.

Chemically sensitive regions, e.g., sensor spots, were produced by dissolving Rhodamine 800 laser dye in Nafion and casting films onto an optical disc. Optical inspection of the dry film was performed to evaluate the optical response of the films to moisture. Typical spectra are shown in FIG. 16. The spectra were collected in absorbance mode using a fiber-optic-based portable spectrograph. As a reference, a spectrum of the film in dry air was used (baseline curve in FIG. 16). Upon exposure to moisture, the absorbance of the film was changed as indicated in FIG. 16, e.g., humid air. The wavelengths of interest (650 and 780 nm) can be easily used with this reagent for moisture determinations.

Figure 17:
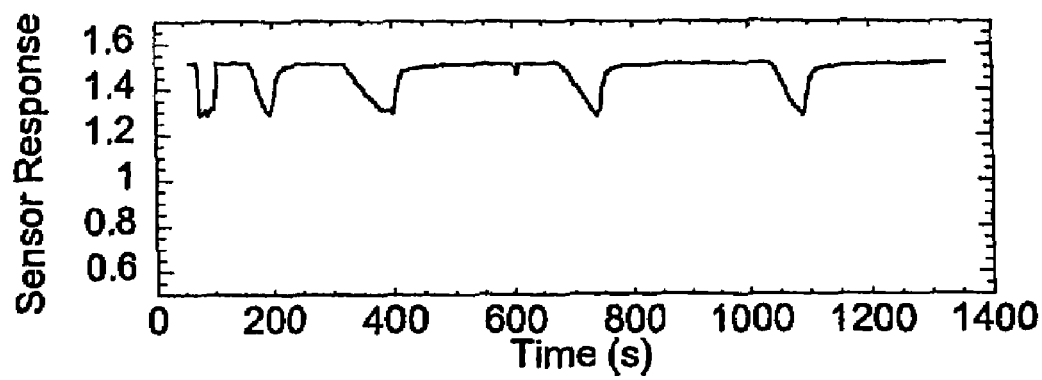
FIG. 17 illustrates signal changes of a sensor in presence of different amounts of ambient water vapor around the sensor (0% RH and 80% RH) as a function of measurement time.

Signal changes of the computer optical drive sensor in the presence of different amounts of ambient water vapor around the sensor, e.g., 0% RH and approximately 80% RH, are presented in FIG. 17. Data collection parameters were set as follows: spot position, 500,000 logical block; waveforms to average, 10; record length 200 Ks/s; and saving frequency, 1 waveform per 5 s. This data demonstrates the practicality of the applications of the optical drive sensors for remote monitoring of chemicals in the ambient.

Figure 18:
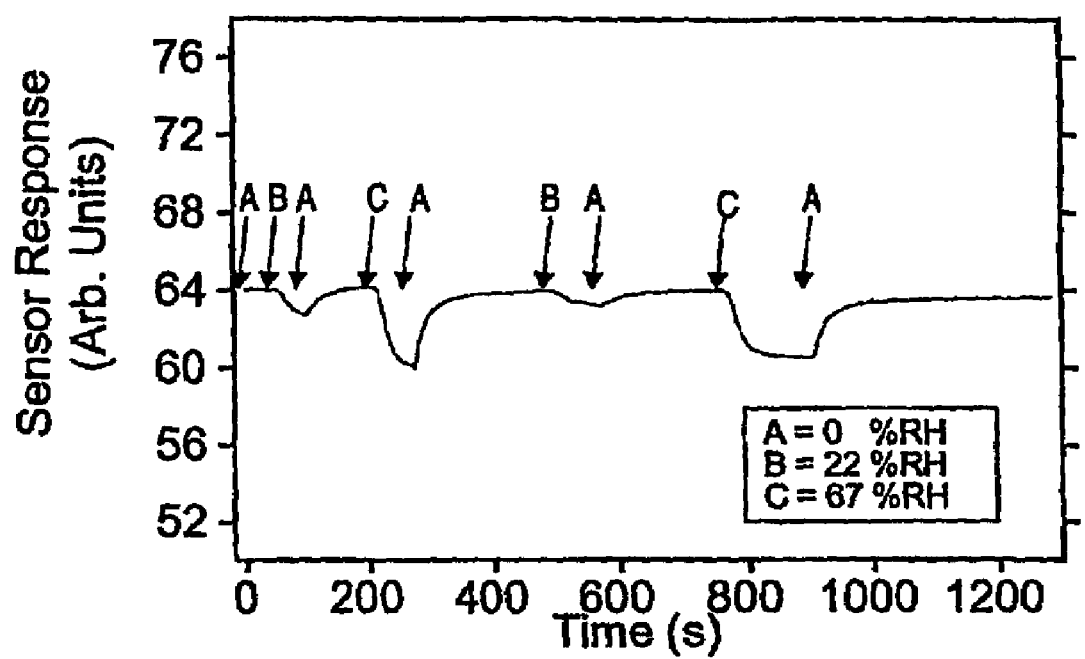
FIG. 18 illustrates results of remote quantification of chemical species as a function of measurement time.

Typical results of remote quantification of chemical species using a remote optical drive sensor are presented in FIG. 18. In these measurements, a Nafion/Rhodamine 800 sensor material positioned on a disc was exposed to variable concentrations of water vapor (0, 22 and 67% RH). Data collection parameters were set as follows: spot position, 330,000 logical block; waveforms to average, 40; record length 200 Ks/s; and saving frequency, 1 waveform per 2 s. When the sensor was exposed to low water-content gas (point A), the sensor signal was the largest as indicated in FIG. 18. Upon increasing concentrations of water vapor, the signal of the sensor was proportionally decreasing. This figure also illustrates the good reproducibility of measurements.

Next, with specific reference to FIGS. 19-22, will be described a system 1900 of remote quantifying of compounds. The system 1900 enables the automatic and remote determination of the quantity of compounds in a fluidic, solid or gel-like substance. System 1900 includes a retrieval device 1904 that moves between a plurality of stations at which certain activities takes place. For example, at station 1902 (FIGS. 19, 20), a DVD 1906 including a plurality of sensor spots 1910 is retrieved by the retrieval device 1904 from a stack 1908 of such DVDs. Retrieval device 1904 may be, for example, a robotic arm having a vacuum pickup feature. Alternatively, retrieval device 1904 may be a robotic arm having an electromagnetic pickup, a mechanical pickup feature (such as multiple fingers that grasp the disk at the outer rim or through the inner hole), or an adhesive pickup feature. The adhesive pickup feature may include a pressure sensitive or thermally sensitive adhesive.

Figure 19:
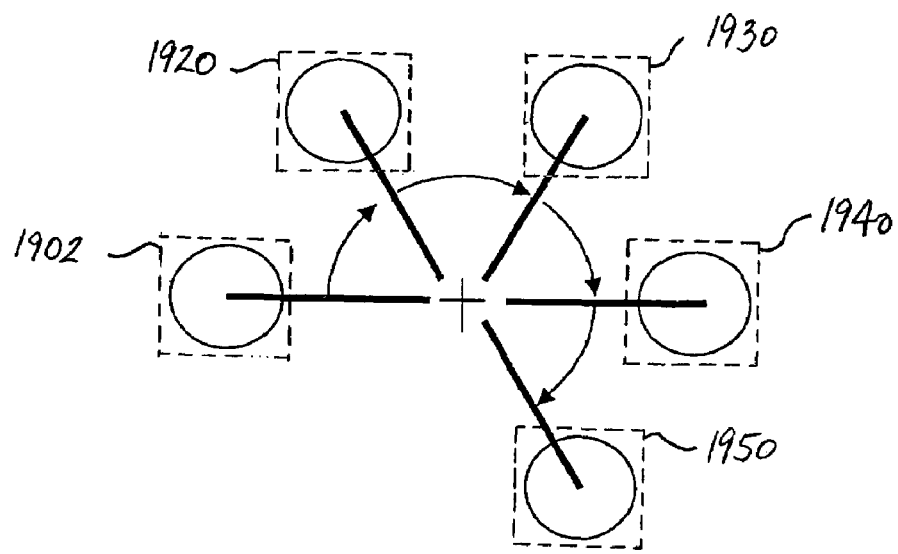
FIG. 19 illustrates a system for remotely quantifying compounds constructed in accordance with an embodiment of the invention.
Figure 20:
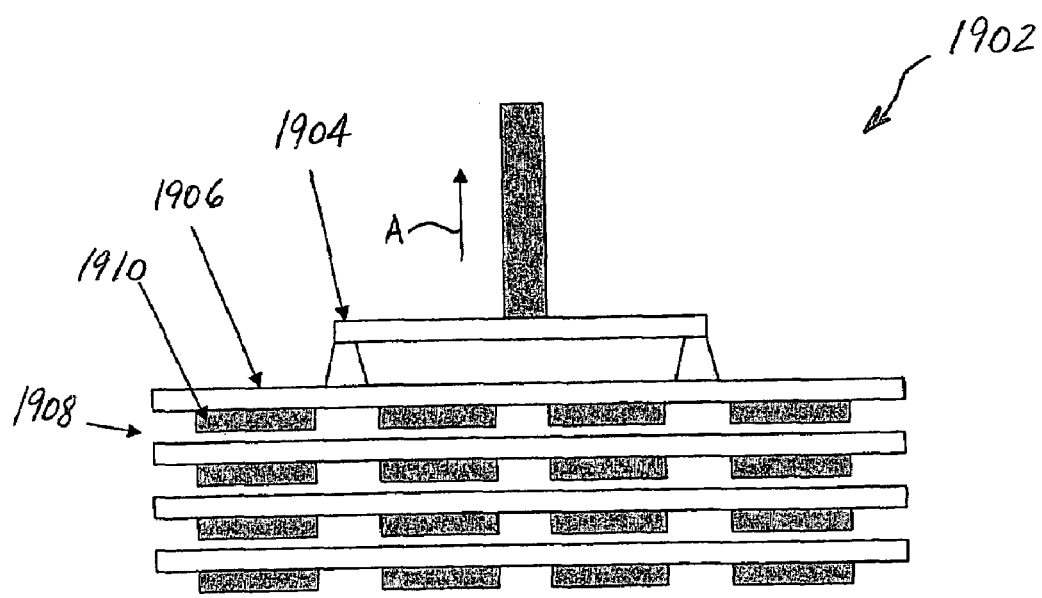
FIG. 20 is a side view of an optical medium retrieving device of the system of FIG. 19 at a station stocked with a plurality of optical medium.
Figure 21:
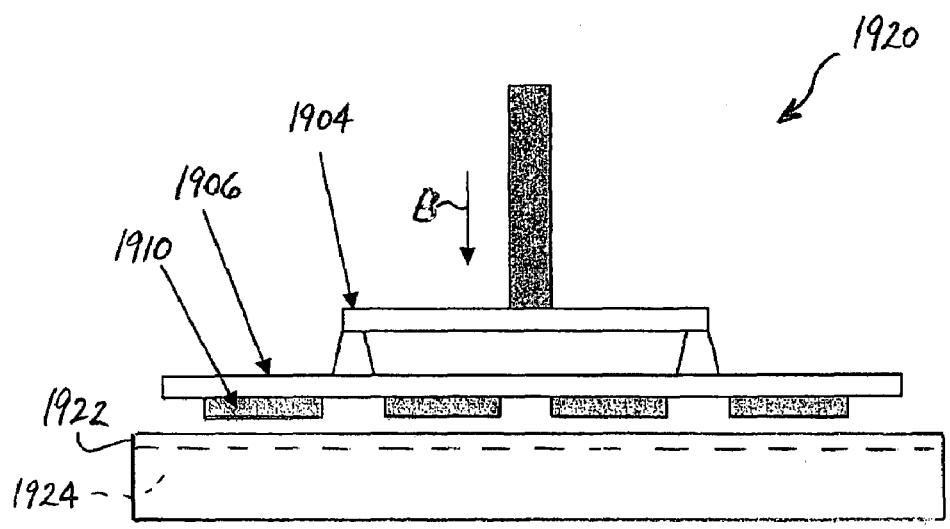
FIG. 21 is a side view of the optical medium retrieving device of the system of FIG. 19 at a station for exposing the optical medium to one or more compounds.
Figure 22:
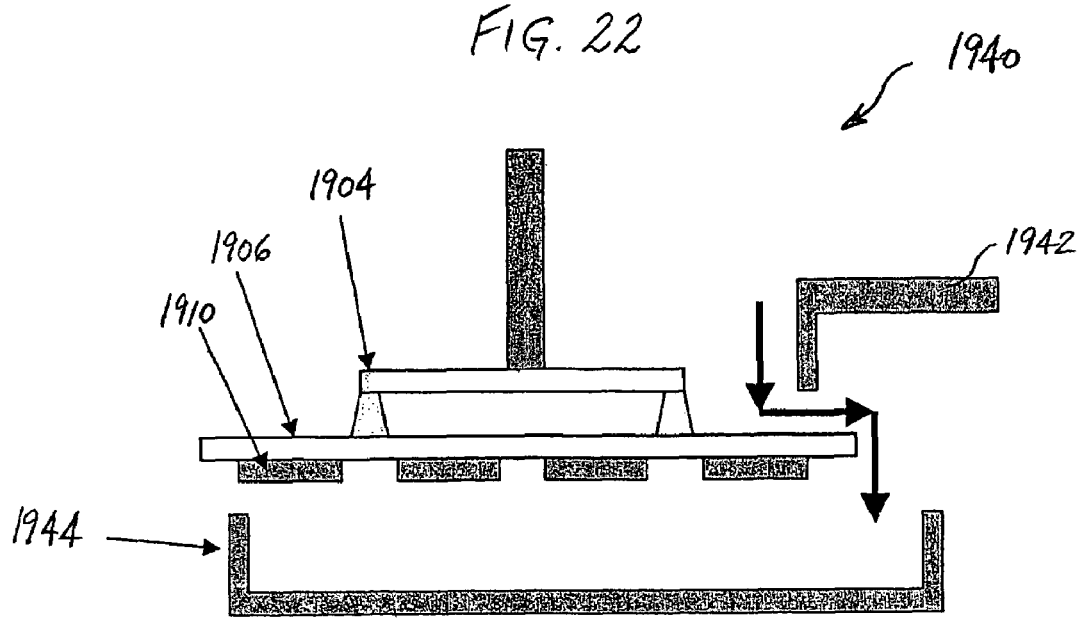
FIG. 22 is a side view of an optical medium retrieving device of the system of FIG. 19 at a station for analyzing the exposed optical medium.

The robotic arm of retrieval device 1904 elevates DVD 1906 in a direction A and then transports DVD 1906 to station 1920 (FIGS. 19, 21). At station 1920, retrieval device 1904 moves DVD 1906 into contact with the fluidic, solid or gel-like material that includes the compounds to be quantified. For example, and as illustrated in FIG. 21, the robotic arm of retrieval device 1904 lowers DVD 1906 in a direction B into contact with a material 1924 located within a vat 1922. Alternatively, instead of dipping DVD 1906 into material 1924, DVD 1906 may be placed in contact with a freely flowing stream of material 1924. Alternatively, the material 1924 may be introduced to the system through an injection system that injects the material 1924 into a preconfigured fluidic sampler that delivers a controlled volume of the material 1924 to each of the sensor spots 1910 contained on the DVD 1906. Sensor spots 1910 are brought into contact with material 1924 so that a determination may be made as to the quantity of a particular compound located within material 1924.

Next, retrieval device 1904 transports DVD 1906 to station 1930 (FIG. 19), at which excess material 1924 is removed from DVD 1906. Utilizing an injection system can minimize the fluid removal step required prior to reading the DVD 1906. After the excess material 1924 has been removed, retrieval device 1904 transports DVD 1906 to station 1904 (FIGS. 19, 22), at which DVD 1906 is optically read. The robotic arm of retrieval device 1904 moves DVD 1906 into an optical drive 1944. The optical drive 1944 may be a DVD optical drive or other suitable reading device. As shown, the optical drive 1944 includes a drive tray covered by a removable door 1942. DVD 1906 is released by the robotic arm of retrieval device 1904 once it is positioned within the drive tray. Door 1942 is closed under computer control and a laser is turned on and positioned so that the optical signals can be recorded.

Figure 23:
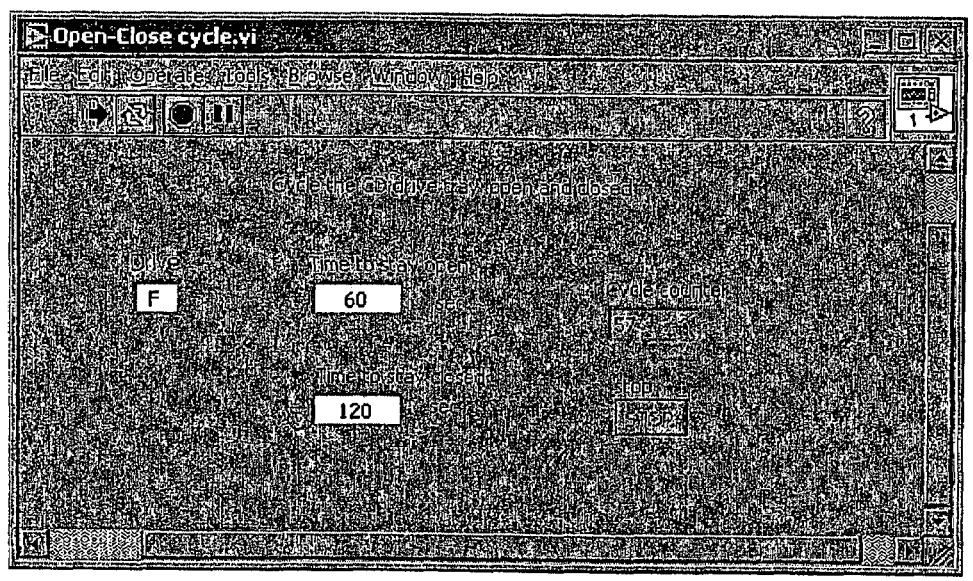
FIG. 23 illustrates a front panel of a LABVIEW® program for automatically controlling an optical medium reader.

Once the optical signals have been recorded, door 1942 is removed and DVD 1906 is picked up again by retrieval device 1904 and moved to a station 1950 (FIG. 19), at which DVD 1906 is discarded. Two sets of automated operations must be executed and synchronized—the movement of retrieval device 1904 and controlling optical drive 1944. Commercially available robots or motion control mechanisms can be utilized as retrieval device 1904 and programmed to move between stations 1902, 1920, 1930, 1940 and 1950. A computer program can be utilized to control optical drive 1944. For example, a program written in LABVIEW® may be uploaded to a personal computer in communication with optical drive 1944. A front panel of the LABVIEW® program is illustrated in FIG. 23. The analysis of the optical drive 1944 may be custom configured to allow time adjusted sequencing to adapt to variation in process loading or sequence timing.

Figure 24:
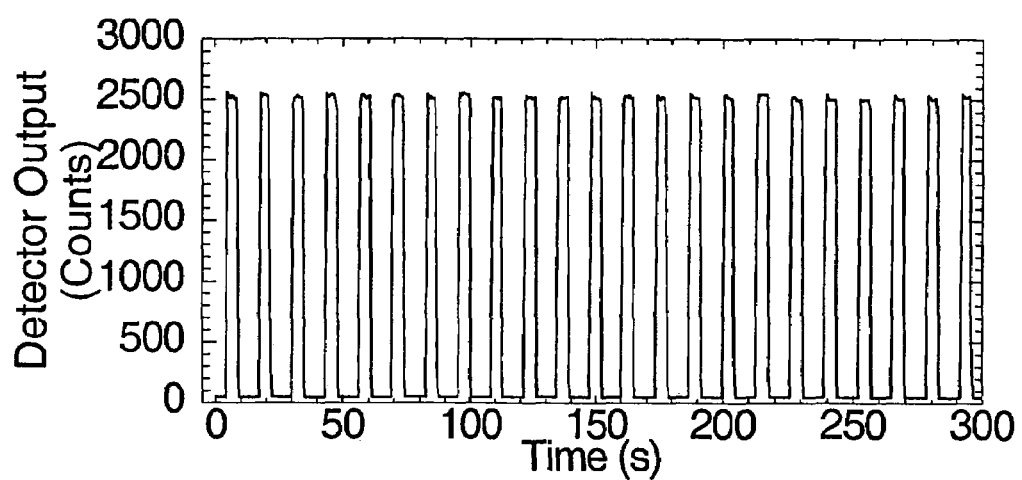
FIG. 24 illustrates a measurement of laser output synchronized with the opening and closing of an optical medium reader.

FIG. 24 illustrates the output of optical drive 1944. As is shown, the laser output turns on and off synchronous with the closing and opening, respectively, of door 1942.

Figure 25:
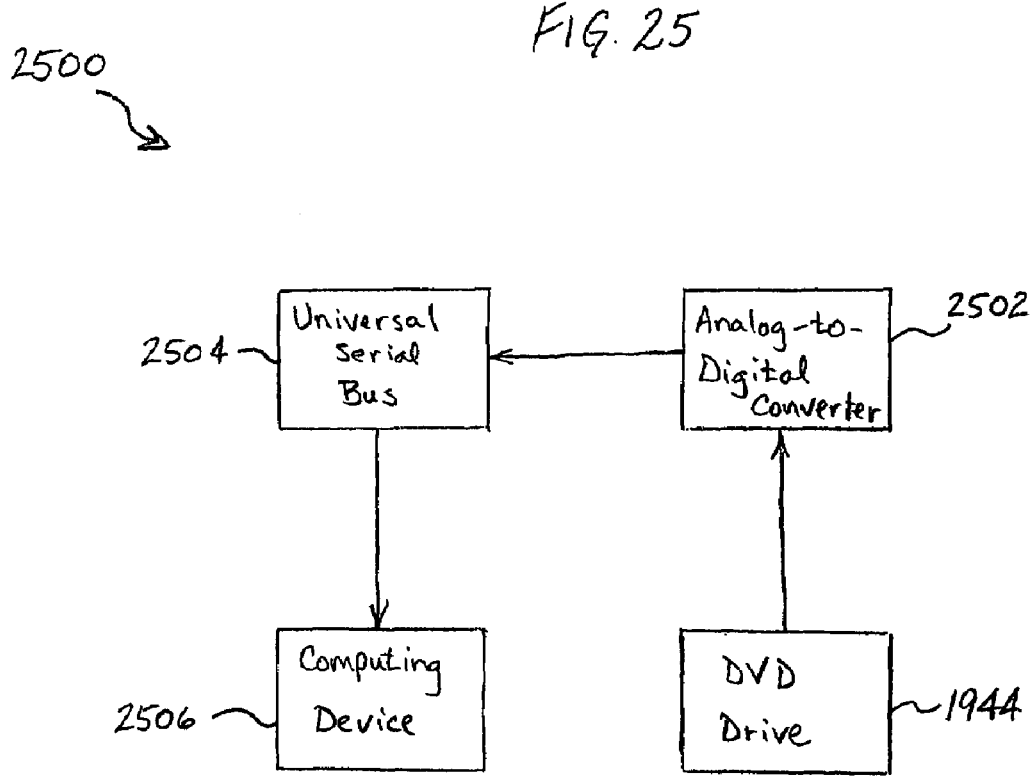
FIG. 25 illustrates a system for quantifying compounds constructed in accordance with another embodiment of the invention.
Figure 26:
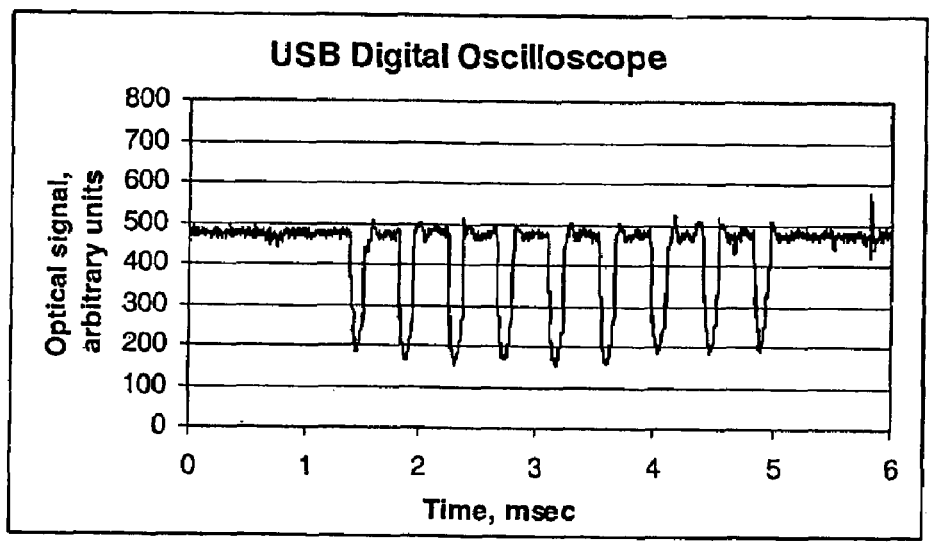
FIG. 26 illustrates output from a USB digital oscilloscope.

With specific reference to FIGS. 25, 26, next will be described an optical reading system that is external to a personal computer or other computing device. While many optical reading devices, such as DVD optical drives, are incorporated within personal computers, such optical reading devices also are available in stand-alone packages. Such optical reading devices can be placed in communication with computing devices through a universal serial bus or through wireless means. As shown in FIG. 25, a DVD drive 1944 is connected to an analog-to-digital converter (ADC) 2502. The ADC 2502 is connected to a universal serial bus 2504, which is connected to a computing device 2506. Alternatively, the DVD drive 1944, ADC 2502 and computing device 2506 can be placed in communication with one another through the use of an Ethernet interface or a wireless connection, such as a Bluetooth wireless connection. FIG. 26 illustrates data collected while scanning nine chemical sensor spots.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

The invention claimed is:

1. An optical media sensor system for quantifying compounds, comprising:
   a robotic arm capable of: transporting an optical medium between a plurality of stations, of transporting the optical medium to an optical drive, and of placing the optical medium in the optical drive to enable an optical media reader to read the optical medium; and
   an optical media reader capable of determining a quantity of at least one compound on said optical medium, and the reading of the optical medium allows time adjusted sequencing to adapt to variation in process loading or in sequence timing.

2. The system of claim 1, wherein said optical media reader is capable of automatically determining a quantity of at least one compound on said optical medium.

3. The system of claim 1, wherein said robotic arm is capable of retrieving a plurality of optical medium in succession from a first station.

4. The system of claim 3, comprising a second station having a source for at least one compound, wherein each said optical medium is exposed to said source.

5. The system of claim 4, wherein the source is provided in a vat.

6. The system of claim 4, wherein the source is provided in a freely flowing stream.

7. The system of claim 4, wherein the source is provided by injecting a volume of the source into a pre-configured fluidic sampler that delivers controlled amounts to each optical medium.

8. The system of claim 4, comprising a third station at which excess amounts of said source are removed from each said optical medium.

9. The system of claim 8, comprising a fourth station at each said optical medium is loaded into and unloaded out of said optical media reader.

10. The system of claim 1, wherein said optical media reader comprises a DVD, CD, BLU-RAY DISC®, super audio CD, or hybrid disk optical drive.

11. The system of claim 1, wherein said robotic arm comprises a vacuum pickup feature.

12. The system of claim 1, wherein said robotic arm comprises an electromagnetic pickup feature.

13. The system of claim 1, wherein said robotic arm comprises an adhesive pickup feature.

14. The system of claim 1, wherein said robotic arm comprises a mechanical pickup feature.

15. An optical media sensor system for quantifying compounds, comprising:
    a robotic arm capable of transporting an optical medium between a first station at which the robotic arm picks up optical medium in succession, a second station at which the optical medium is exposed to a source of the compounds, a third station at which excess amounts of the source are removed, a fourth station at which the optical medium is read, and a fifth station at which the optical medium is discarded; and
    an optical media reader capable of determining a quantity of at least one compound on said optical medium at the fourth station, and of reading the optical medium allowing time adjusted sequencing to adapt to variation in process loading or in sequence timing.

16. The system of claim 15, wherein the source is provided in a vat.

17. The system of claim 15, wherein the source is provided in a freely flowing stream.

18. The system of claim 15, wherein the source is provided by injecting a volume of the source into a pre-configured fluidic sampler that delivers controlled samples to each optical medium.

19. The system of claim 15, wherein said robotic arm comprises a vacuum pickup feature.

20. The system of claim 15, wherein said robotic arm comprises an electromagnetic pickup feature.

21. The system of claim 15, wherein said robotic arm comprises an adhesive pickup feature.

22. The system of claim 15, wherein said robotic arm comprises a mechanical pickup feature.

23. A system for optically determining the quantity of one or more compounds on one or more sensors, comprising:
    a computing device;
    an optical drive located external to said computing device, wherein said optical drive comprises an optical media reader that is capable of optically reading an optical medium upon which are located the one or more sensors and wherein said optical drive is in communication with said computing device; and
    a robotic arm that is capable of transporting the optical medium to the optical drive, and of placing the optical medium in the optical drive to enable the optical media reader to read the optical medium, and the reading of the optical medium allows time adjusted sequencing to adapt to variation in process loading or in sequence timing.

24. The system of claim 23, wherein said optical drive comprises a DVD, CD, BLU-RAY DISC®, super audio CD, or hybrid disc optical drive.

25. The system of claim 23, wherein said optical drive communicates with said computing device though a universal serial bus.

26. The system of claim 23, wherein said optical drive communicates with said computing device though an Ethernet interface.

27. The system of claim 23, wherein said optical drive communicates with said computing device though a Bluetooth communication mechanism.

28. The system of claim 23, further comprising an analog-to-digital converter in communication with said optical drive and said computing device.

29. A method for determining the quantity of one or more compounds on one or more sensors, comprising:
    remotely retrieving an optical medium having one or more sensors from a first station;
    exposing the optical medium to a source of the compounds at a second station;
    transporting the optical medium to the optical drive, placing the optical medium in the optical drive, and automatically enabling the optical drive to read the optical medium; and
    reading the optical medium in an optical drive, wherein the reading of the optical medium is custom configured to allow time adjusted sequencing to adapt to variation in process loading or sequence timing.

30. The method of claim 29, wherein said remotely retrieving comprises remotely retrieving the optical medium with a robotic arm.

31. The method of claim 30, wherein said remotely retrieving comprises picking up the optical medium with a vacuum pickup.

32. The method of claim 30, wherein said remotely retrieving comprises picking up the optical medium with an electromagnetic pickup.

33. The method of claim 30, wherein said remotely retrieving comprises picking up the optical medium with an adhesive pickup.

34. The method of claim 30, wherein said remotely retrieving comprising picking up the optical medium with a mechanical pickup.

35. The method of claim 29, wherein said exposing comprises dipping the optical medium into a vat containing the source of the compounds.

36. The method of claim 29, wherein the source of the compounds is a freely flowing source and said exposing comprises contacting the optical medium with the freely flowing source.

37. The method of claim 29, wherein the source is provided by injecting a volume of the source into a pre-configured fluidic sampler that delivers controlled amounts to each optical medium.

38. The method of claim 29, further comprising after said remotely retrieving step removing excess amounts of the source from the optical medium.

39. The method of claim 29, further comprising after said reading step discarding the optical medium.

40. A method for determining the quantity of one or more compounds on one or more sensors, comprising:

remotely retrieving an optical medium having one or more sensors from a first station;

exposing the optical medium to a source of the compounds at a second station;

removing excess amounts of the source from the optical medium at a third station;

transporting the optical medium to an optical drive to place the optical medium in the optical drive and to enable the optical drive to read the optical medium;

reading the optical medium in the optical drive at a fourth station, wherein the reading of the optical medium is custom configured to allow time adjusted sequencing to adapt to variation in process loading or sequence timing.

41. The method of claim 40, wherein said remotely retrieving comprises remotely retrieving the optical medium with a robotic arm.

42. The method of claim 40, wherein said exposing comprises dipping the optical medium into a vat containing the source of the compounds.

43. The method of claim 40, wherein the source of the compounds is a freely flowing source and said exposing comprises contacting the optical medium with the freely flowing source.

44. The method of claim 40, wherein said reading comprises placing the optical medium in the optical drive and enabling the optical drive to read the optical medium.

45. The method of claim 40, further comprising discarding the optical medium at a fifth station.

* * * * *